(12) United States Patent
Li et al.

(10) Patent No.: US 7,122,149 B2
(45) Date of Patent: Oct. 17, 2006

(54) APPARATUS AND METHOD FOR CONTINUOUS DEPYROGENATION AND PRODUCTION OF STERILE WATER FOR INJECTION

(75) Inventors: Lixiong Li, Panama City, FL (US); Timothy J. Campbell, Panama City, FL (US); Robert K. Nichols, Jr., Panama City, FL (US); Kristopher S. Cozart, Panama City, FL (US)

(73) Assignee: Applied Research Associates, Inc., Albuquerque, NM (US)

( * ) Notice: Subject to any disclaimer, the term of this patent is extended or adjusted under 35 U.S.C. 154(b) by 125 days.

(21) Appl. No.: 10/618,133

(22) Filed: Jul. 11, 2003

(65) Prior Publication Data

US 2004/0109788 A1    Jun. 10, 2004

Related U.S. Application Data

(60) Provisional application No. 60/395,377, filed on Jul. 12, 2002.

(51) Int. Cl.
*C02F 1/02* (2006.01)
(52) U.S. Cl. .................. 422/26; 210/103; 210/130; 210/134; 210/149; 210/181; 210/182; 210/195.2; 210/258; 210/259; 210/416.3; 210/428; 210/900
(58) Field of Classification Search ............... 210/181, 210/182, 194, 195.1, 195.2, 418, 428, 433.1, 210/900, 103, 130, 134, 149, 258, 259, 416.3; 165/156; 422/26
See application file for complete search history.

(56) References Cited

U.S. PATENT DOCUMENTS 1,027,381 A * 5/1912 Fox .................. 401/87

| | | |
|---|---|---|
| 2,362,724 A | 11/1944 | Shea |
| 3,068,794 A | 12/1962 | Morris et al. |
| 3,249,229 A * | 5/1966 | Kasten .................. 210/195.1 |
| 3,601,378 A | 8/1971 | Hurst |

(Continued)

FOREIGN PATENT DOCUMENTS

GB        2002736 A  *  2/1979

(Continued)

OTHER PUBLICATIONS

W. Dickinson Burrows and James H. Nelson, IV Fluidmakers: Preparation of Sterile Water for Injection in a Field Setting, Journal of Parenteral Science & Technology, May-Jun. 1993, pp. 124-129, vol. 47 No. 3.

(Continued)

*Primary Examiner*—Matthew O. Savage
(74) *Attorney, Agent, or Firm*—Ostrager Chong Flaherty & Broitman

(57) ABSTRACT

A fluid processor, suitable for the production of sterile water for injection, having a processor assembly and a process control system comprising a pump, a flow splitter, flow restrictors and a pressure relief valve. In a preferred embodiment, the processor assembly comprises a heat exchanger, a reactor and a heater arranged in a nested configuration. The preferred embodiment of the present invention also include a treatment assembly having a combination of filter, reverse osmosis and ion exchange devices and further incorporates an assembly and method allowing for the in situ sanitization of the fluid processor during cold start and shutdown to prevent bacteria growth during storage of the fluid processor. The fluid processor may include an electronic control system comprising a touch screen operator interface, a programmable logic controller and sensors for measuring temperature, pressure, flow rate, conductivity and endotoxin level.

52 Claims, 17 Drawing Sheets

PROCESSOR ASSEMBLY

U.S. PATENT DOCUMENTS

| | | | |
|---|---|---|---|
| 3,648,438 | A | 3/1972 | Arbogast |
| 3,860,494 | A | 1/1975 | Hickman |
| 3,870,033 | A | 3/1975 | Faylor et al. |
| 4,069,153 | A | 1/1978 | Gunther |
| 4,070,289 | A | 1/1978 | Akcasu |
| 4,072,610 | A * | 2/1978 | Gow et al. .............. 210/90 |
| 4,182,354 | A | 1/1980 | Bergstedt |
| 4,261,834 | A | 4/1981 | deWinter |
| 4,276,177 | A | 6/1981 | Smith |
| 4,381,239 | A | 4/1983 | Chibata et al. |
| 4,495,067 | A | 1/1985 | Klein et al. |
| 4,547,289 | A | 10/1985 | Okano et al. |
| 4,548,716 | A | 10/1985 | Boeve |
| 4,610,790 | A | 9/1986 | Reti et al. |
| 4,648,978 | A | 3/1987 | Makinen et al. |
| 4,673,733 | A | 6/1987 | Chandra et al. |
| 4,752,389 | A | 6/1988 | Burrows |
| 4,759,909 | A | 7/1988 | Joslyn |
| 4,772,390 | A | 9/1988 | Kawai et al. |
| 4,810,388 | A | 3/1989 | Trasen |
| 4,833,888 | A | 5/1989 | Kerner et al. |
| 4,858,643 | A | 8/1989 | Vavra et al. |
| 4,883,596 | A | 11/1989 | Agui et al. |
| 4,909,942 | A | 3/1990 | Sato et al. |
| 4,913,827 | A | 4/1990 | Nebel |
| 4,935,150 | A | 6/1990 | Iida et al. |
| 4,958,658 | A | 9/1990 | Zajac |
| 5,021,391 | A | 6/1991 | Agui et al. |
| 5,026,258 | A | 6/1991 | Mosley |
| 5,032,265 | A | 7/1991 | Jha et al. |
| 5,104,546 | A | 4/1992 | Filson et al. |
| 5,147,532 | A * | 9/1992 | Leek, Jr. .............. 210/97 |
| 5,166,123 | A | 11/1992 | Agui et al. |
| 5,188,020 | A | 2/1993 | Rockenfeller et al. |
| 5,202,246 | A | 4/1993 | Kruse et al. |
| 5,242,595 | A | 9/1993 | Morgart et al. |
| 5,279,821 | A | 1/1994 | Hirayama et al. |
| 5,401,421 | A | 3/1995 | Blum |
| 5,401,499 | A | 3/1995 | Hirayama et al. |
| 5,498,409 | A | 3/1996 | Hirayama et al. |
| 5,503,735 | A * | 4/1996 | Vinas et al. .............. 210/87 |
| 5,520,816 | A * | 5/1996 | Kuepper .............. 210/649 |
| 5,717,303 | A | 2/1998 | Engel |
| 5,851,293 | A | 12/1998 | Lane et al. |
| 5,880,438 | A | 3/1999 | Parrini et al. |
| 5,917,022 | A | 6/1999 | Davies |
| 5,928,481 | A | 7/1999 | Briggs |
| 5,949,958 | A | 9/1999 | Naperkowski et al. |
| 6,030,436 | A | 2/2000 | Barclay |
| 6,086,822 | A | 7/2000 | Trinidad |
| 6,094,523 | A | 7/2000 | Zelina et al. |
| 6,167,951 | B1 | 1/2001 | Couch et al. |
| 6,247,903 | B1 | 6/2001 | Wong |
| 6,406,273 | B1 | 6/2002 | Wong |
| 6,485,649 | B1 * | 11/2002 | Terava et al. .............. 210/636 |
| 6,585,890 | B1 | 7/2003 | Li et al. |
| 6,679,988 | B1 * | 1/2004 | Gsell .............. 210/181 |
| 2001/0050215 | A1 | 12/2001 | Li et al. |
| 2002/0132341 | A1 * | 9/2002 | Benedict .............. 435/366 |
| 2003/0164339 | A1 | 9/2003 | Li et al. |

FOREIGN PATENT DOCUMENTS

| | | |
|---|---|---|
| WO | WO 91/04086 | 4/1991 |

OTHER PUBLICATIONS

Andrew W. Collentro, Pharmaceuticals—Pratical Microbial Control Techniques for Pharmaceutical Water Purification Systems, Ultrapure Water, Mar. 2002, pp. 53-60.

Kiyoshi Tsuji an Susan Harrison, Dry-Heat Destruction of Lipopolysaccharide: Dry-Heat Destruction Kinetics, Appl. Environ. Microb., Nov. 1978, pp. 710-714, vol. 38 No. 5.

United States Food and Drug Administration (FDA), ITG Subject: Heat Exchangers to Avoid Contamination, Inspection Technical Guide (ITG) No. 34, Jul. 31, 1979, pp. 1-3, at www.fda.gov/ora/inspect_ref/itg/itg34.html (last visited Mar. 29, 1999).

United States Food and Drug Administration (FDA), ITG Subject: Pyrogens, Still a Danger, Inspection Technical Guide No. 32, Jan. 12, 1979, pp. 1-3, at www.fda.gov/ora/inspect_ref/itg/itg32.html (last visited Mar. 29, 1999).

United States Food and Drug Administration (FDA), Guide to Inspections of High Purity Water Systems, pp. 1-9, at www.fda.gov/ora/inspect_ref/igs/high.html (last visited Mar. 24, 1999).

Kyoshi Tsuji and A.R. Lewis, Dry-Heat Destruction of Lipopolysaccharide: Mathematical Approach to Process Evaluation, Appl. Environ. Microb., Nov. 1978, pp. 715-719, vol. 36 No. 5.

Hans Traeger, Pharmaceuticals—The Presence of Bacteria, Endotoxins, and Biofilms in Pharmaceutical Water, Ultrapure Water, Mar. 2003, pp. 17-22.

Alex Konopka, Pharmaceuticals—Current Issues and System Design Considerations Affecting Pharmaceutical Water Systems, Ultrapure Water, Mar. 2002, pp. 22-30.

David H. Paul, Back to Basics—The Combining of Reverse Osmosis and Ion Exchange, Ultrapure Water, Jul./Aug. 2002, pp. 38-40.

United States Food and Drug Administration (FDA) ITG Subject: Bacterial Endotoxins/Pyrogens, Inspection Technical Guide (ITG) No. 40, Mar. 20, 1985, pp. 1-10, at www.fda.gov/ora/inspect_ref/itg/itg40.html (last visited Mar. 24, 1999).

United States Food and Drug Administration (FDA), ITG Subject: Water for Pharmaceutical Use, Inspection Technical Guide (ITG) No. 46, Dec. 31, 1986, pp. 1-4, at www.fda.gov/ora/inspect_ref/itg/itg46.html (last visited Oct. 9, 2003.

European Patent Office Abstract—Pyrogen Adsorbent and Removal of Pyrogen Using the Same, JP 4-114661, Apr. 15, 1992.

European Patent Office Abstract—Removal of Pyrogen From Resin Carrier, JP 1-203046 Aug. 15, 1989.

European Patent Office Abstract—Removal of Pyrogen From Aqueous Solution, JP 59-112888, Jun. 29, 1984.

European Patent Office Abstract—Removal of Pyrogen in Water, JP 57-171403, Oct. 22, 1982.

* cited by examiner

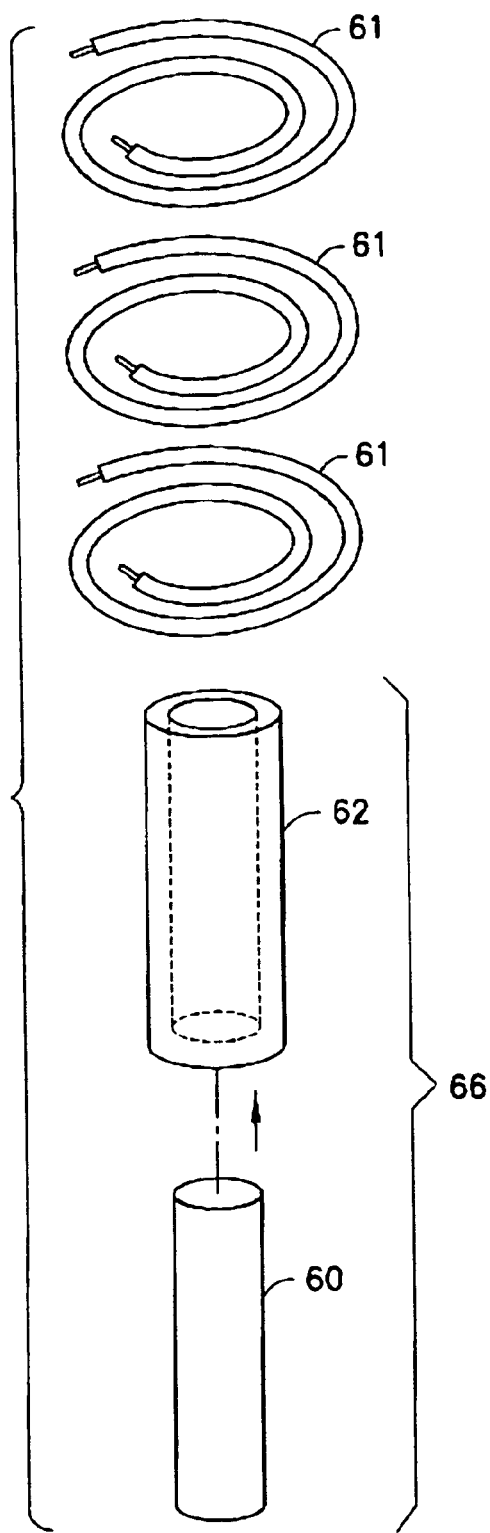
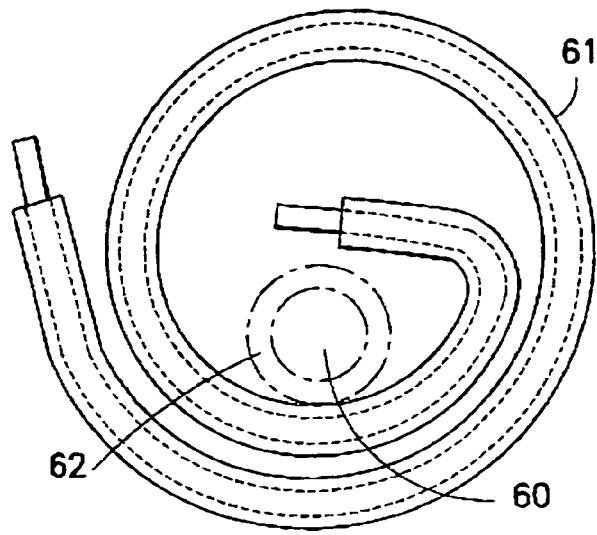
FIG.6B
FIG.6A

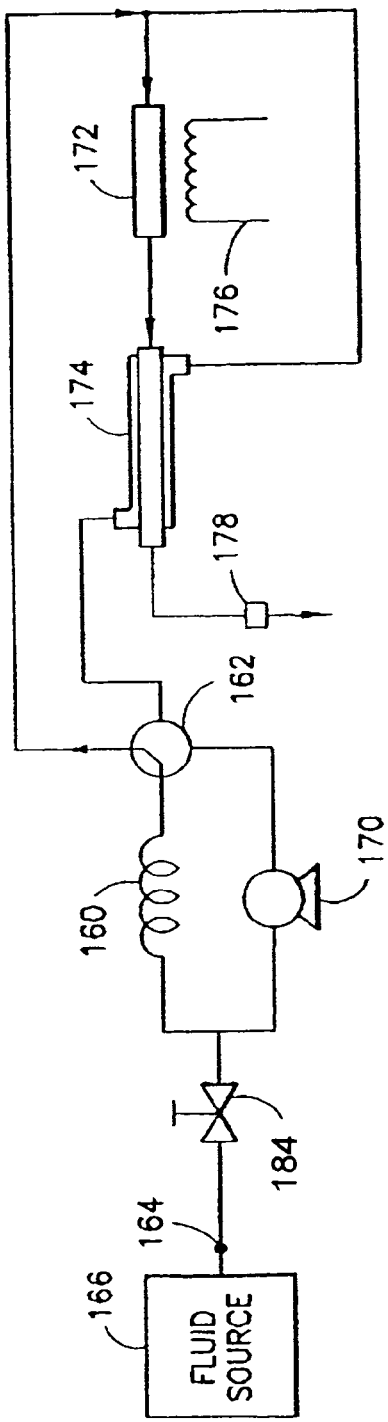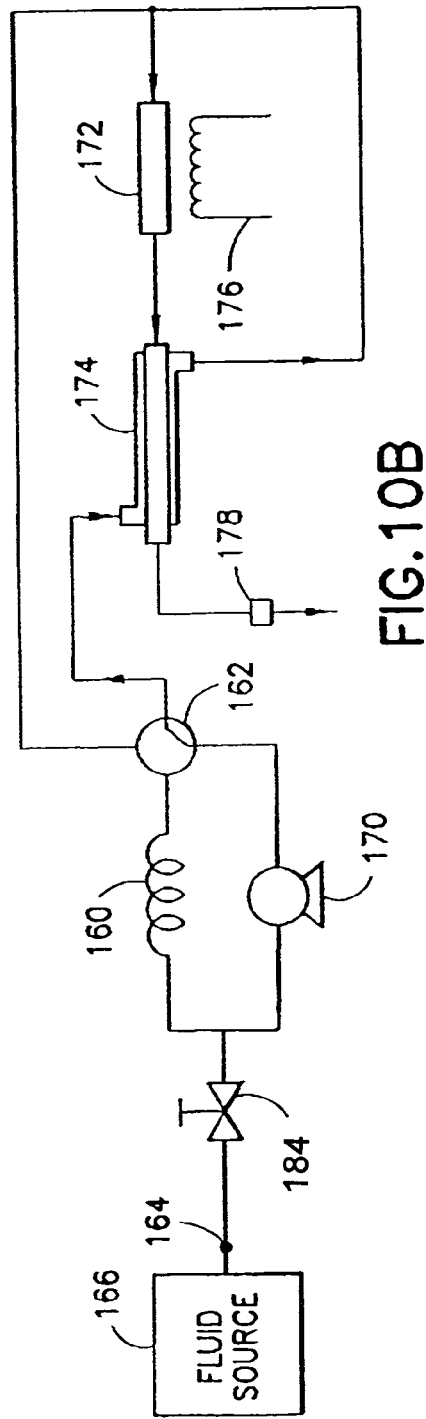

APPARATUS AND METHOD FOR CONTINUOUS DEPYROGENATION AND PRODUCTION OF STERILE WATER FOR INJECTION

PRIORITY CLAIM

This non-provisional application claims priority from United States Provisional Patent Application Ser. No. 60/395,377 filed on Jul. 12, 2002.

The U.S. Government has a paid-up license in this invention and the right, in limited circumstances, to prepare the patent owner to license others on reasonable terms as provided for by the terms of contracts N00014-99-M-0254 and N00014-01-C-0101 awarded by the Office of Naval Research, United States Navy.

FIELD OF THE INVENTION

This invention generally relates to fluid processors, more particularly to a fluid processor having a process control system that uses an improved apparatus and method for process control and which is suitable for the depyrogenation and production of sterile water for injection using a hydrothermal process.

BACKGROUND ART

Sterile water for injection (SWFI) is an essential component in reconstituting freeze-dried blood products and in the preparation of "parenteral solutions" (i.e., solutions introduced into the human body such as intravenous fluids). The production of SWFI is a significant problem for medical personnel operating under field conditions such as in combat or during disaster relief operations. The solution of this problem requires a compact, reliable, and automatic system that can continuously produce SWFI from available water sources under field conditions. For example, an efficient and compact fluid processor is essential to meet the field deployment requirements for a system to produce SWFI as set forth in the United States Navy's requirements for a SWFI generator. See, RFP Navy STTR N99-T008. Such a fluid processor should also incorporate a heat sterilization operation as the final processing step as preferred by the United States Food and Drug Administration ("FDA"). See, Inspectors Technical Reference No. 40, FDA (1985). This thermal treatment feature would have a positive impact on obtaining FDA approval of such a device. In addition, such a system must be easy to maintain and operate, and have low energy requirements for operation.

In order to meet regulatory requirements, (see, United States Pharmacopoeia XXIV) SWFI must be sterile (i.e., free of all living micro-organisms) and free of particulate matter, oxidizable substances, dissolved gases, metals and electrolytes. In addition, SWFI must be rendered free of pyrogens ("depyrogenated"). Also known as bacterial endotoxins, pyrogens are metabolic products of living micro-organisms or dead micro-organisms. Chemically, pyrogens are lipopolysaccharides ("LPS"). The term "pyrogen" (i.e., fever-producing agent) is derived from the fact that if a parenteral product containing pyrogens is injected into a patient, a rapid rise in body temperature occurs after a latent period of about one hour, followed by chills, headache, and malaise. Pyrogens lose little of their potency over the years and effective depyrogenation requires high temperatures and long holding times.

Sterilization and depyrogenation of water can be accomplished by physical methods (e.g., heat), chemical agents (e.g., ethylene oxide, formaldehyde, alcohol, and ozone), radiation (e.g., ultraviolet radiation) or mechanical methods (e.g., filtration). Present systems for manufacturing SWFI generally employ distillation or reverse osmosis ("RO") methods for depyrogenation in combination with additional treatment steps, typically involving active carbon filters, deionizers, and ultrafiltration filters. However, distillation and RO systems only separate pyrogens from water. Pyrogen residues remain in these systems in the form of distillation still residue or reverse osmosis retentate. Thus, these systems must be continually or periodically purged in order to remove these pyrogen residues. This requirement makes these systems unsuitable for use under field conditions. These systems also have other disadvantages that make them unsuitable for use in the field.

Distillation systems are generally highly energy intensive and require a number of system components such as heat exchangers, evaporators, condensers, and vapor compressors. These components are either bulky or difficult to use or maintain in the field. Also, recuperating thermal energy is the most critical factor in a practical distillation system. Consequently, distillation systems generally use vapor compression and plate-and-frame heat exchangers since this combination is effective in improving the thermal efficiency of conventional distillation processes. However, plate-and-frame heat exchangers do not comply with the heat exchanger design guidelines established by the FDA for continuous production of SWFI. See, Inspectors Technical Guide No. 34, FDA (1979). Therefore, the product water produced using heat exchangers other than those recommended by FDA must be collected and batch validated before use. See, Inspectors Technical Guide No. 34, FDA (1979).

As for RO systems, these require periodic changing of the filters in order to remain effective. Moreover, RO filters are not entirely satisfactory. In particular, RO systems lack a final heat sterilization capability that is currently required for approval by the FDA. Generally, RO systems are water for injection ("WFI") systems that operate at ambient temperatures. Such relatively low temperature systems present a problem because many objectionable micro-organisms that are good sources of endotoxins grow well in cold WFI. See, Inspectors Technical Guide No. 40, FDA (1985). Thus, to prevent microbial growth WFI is usually produced in a continuously circulating system maintained at an elevated temperature that must be at least 80° C. to be considered as acceptable. See, Inspectors Technical Guide No. 46, FDA (1986). Other RO systems require the use of special filters. For example, U.S. Pat. No. 4,810,388 to Trasen and U.S. Pat. No. 5,032,265 to Jha, et al. both disclose depyrogenating water using RO and then passing the water through a sterilizing filter instead of using heat in order to sterilize the water. Current practice in the U.S. to produce SWFI by the RO method requires a two-stage RO separation process (in series) followed by ultra-violet ("UV") sterilization. The foregoing limitations make RO systems unsuitable for a SWFI production system to be used in the field.

Other depyrogenation methods require adding substances (i.e., "depyrogenating agents") to water in order to depyrogenate the water. However, these depyrogenating agents have to be removed from the water after completion of the depyrogenation process. This makes this method more complicated and not easy to use in the field. For example, U.S. Pat. No. 4,935,150 to Iida, et al. discloses adding calcium salt to water to remove pyrogens and then later removing the resulting precipitate. U.S. Pat. No. 4,648,978 to Makinen, et al. discloses depyrogenating water by adding an oxidant selected from the group consisting of hydrogen peroxide and ozone and heating the solution. The resulting solution requires further processing to remove the oxidant.

Another method of depyrogenation involves passing water through materials that adsorb pyrogens. See, for example, U.S. Pat. No. 5,498,409 to Hirayama, et al. and U.S. Pat. No. 5,166,123 to Agui, et al. However, this method has the same disadvantage as apparatus that use distillation and RO methods in that the use of adsorbents only separates pyrogens from water. The concentrated pyrogen (hereafter, "isolated pyrogen") that has adhered to the adsorbents still has to be disposed, purged, or destroyed (i.e., chemically altered or degraded to permanently lose their potency as pyrogens).

Pyrogens in water can also be destroyed by subjecting the water to high temperature under pressure. This method of water treatment is called hydrothermal processing ("HTP"). U.S. Pat. No. 4,070,289 to Akcasu discloses a method of depyrogenation by heating water in a sealed, pressurized container. However, Akcasu does not allow for the continuous production of depyrogenated water. At most, the process disclosed in Akcasu can be operated as a "semi-batch process". That is, two containers are operated in parallel wherein external cooling water flows between the two containers in series, cooling down the treated water in the first container and subsequently pre-heating the water to be treated in the next container. In addition to being unable to continuously produce depyrogenated water, the foregoing configuration of containers results in a fluid processor that is bulky and not suitable for use in the field. U.S. Pat. No. 6,167,951 to Couch et al. discloses a depyrogenation process involving heating water followed by catalytic wet air oxidation. However, the heating step requires a specially designed heat exchanger rather than a standard heat exchanger. This makes the process more complicated and expensive. Further, the oxidizing step requires exposing the heated water to a wet oxidation catalyst in a reactor with sufficient air or oxygen. However, contacting water with the catalyst could result in the dissolution of certain components of the catalyst into the water being processed, and hence increasing the risk of contaminating the resulting product water. This is of particular concern if the intention is to produce SWFI. Furthermore, the wet air oxidation process requires high-pressure air or oxygen that must be generated by a compressor or other similar source. This would increase the complexity of an SWFI production system to be used in the field.

There are other depyrogenation methods involving high-temperature processing steps. However, these require additional treatment of the heated water in order to remove pyrogens. For instance, U.S. Pat. No. 6,485,649 to Tereva, et al. discloses a process involving sterilization of water by heating water and the passing the heated water through a thermally stable filter to remove pyrogens. Such apparatus are not satisfactory for field use since they require multiple steps to depyrogenate water or require frequent changing of filters to ensure depyrogenation. This makes them more complicated and difficult to maintain in the field.

Apparatus used for producing SWFI must also be sanitized on startup to eliminate any micro-organisms that may have developed in the apparatus during storage. These apparatus must also be properly shut down and sealed after use in order to prevent contamination and the growth of micro-organisms during storage. Steam and dry heat are widely used means of for sterilizing SWFI equipment. Generally, present systems for producing SWFI require disassembly and sanitization of the individual components to ensure proper sanitization. This makes it difficult to use these apparatus under field conditions where proper sanitizing equipment or facilities are not readily available.

The processing of fluids (e.g., depyrogenating water) also requires a process control system. This is because any chemical or physical process, particularly the ones used in the field, is ideally operated in a convergingly stable domain such that minimum operator intervention is required. The stability of a fluid process is commonly characterized by four basic variables: temperature, pressure, flow rate, and level of the fluid being processed. In general, the critical process parameters for a high-pressure fluid processor are pressure, flow rate and temperature.

Current process control systems fall into two categories. In the first category are process control systems such as the system shown in FIG. I which are precise, but which require elaborate and complex sensors 10 and control valves 12, 14. The final control element for flow rate and pressure is generally an automatic control valve 14 having a throttling action operated electrically or pneumatically in response to readings from a sensor 10. Automatic control valves are relatively bulky, complex, and prone to mechanical failure. Thus, a system equipped with automatic control valves is not compact, robust, simple to operate or maintain. In the second category are process control systems that use simple mechanisms but which are not precise or reliable and which require frequent adjustment. For example, FIG. 2 shows a simple pressure-control system that does not have pressure sensor feedback and which uses a pressure-relief valve 16 (typically a spring-loaded type) in place of an automatic control valve. This system often shows pressure fluctuation and/or drifting, and requires frequent adjustment of the pressure relief valve.

In order to overcome the disadvantages of the prior art, it is the principal object of the present invention to provide an apparatus and related method for hydrothermal production of SWFI that is compact, reliable, easy to maintain and operate and which has low energy requirements. In particular, it is a specific object to obtain an SWFI fluid processor having a reliable, simple and compact process control system that is suitable for the continuous depyrogenation and production of SWFI using HTP without producing isolated pyrogen or requiring additional steps for depyrogenation. It is the further object to obtain an SWFI fluid processor that has built-in features and simple procedures for both sanitizing the system during a cold start, and for maintaining system sterility during shutdown, storage, and restart.

SUMMARY OF THE INVENTION

The present invention encompasses a fluid processor comprising a pump for drawing a fluid from a fluid source through a fluid inlet and pressurizing the fluid, a processor assembly for processing the fluid, and a process control system. The process control system has a flow splitter for diverting a portion of the fluid from the pump in order to form a recirculating loop, a first flow restrictor for receiving the fluid diverted by fluid splitter and directing the diverted fluid to the fluid inlet, a pressure relief valve disposed along the recirculating loop, and a second flow restrictor disposed downstream of the processor assembly to provide a back-pressure to the fluid in the fluid processor. The flow splitter, first flow restrictor, the second flow restrictor and the pressure relief valve are constructed and arranged to coact with each other so as to control the pressure and flow rate of the fluid in the fluid processor. The invention also includes a method for controlling the fluid processor. The method comprises drawing a fluid from a fluid source through a fluid inlet, pressurizing the fluid, diverting a portion of the pressurized fluid back to the fluid inlet to form a recirculating loop, controlling the flow rate and pressure of the fluid in the recirculating loop using a first flow restrictor and a pressure relief valve, and applying a backpressure to the fluid in the fluid processor using a second flow restrictor.

The present invention further includes a treatment assembly having a combination of a filter and other devices such as reverse osmosis and ion exchange devices. The treatment assembly removes suspended and dissolved solids (e.g., particulate matter, oxidizable substances), dissolved gases, metals and electrolytes from the fluid so that fouling in the fluid processor can be minimized. The treatment assembly also ensures that the resulting product of the fluid processor meets regulatory standards for SWFI.

A further aspect of the invention is an electronic control system for controlling the fluid processor and make it convenient for an untrained person to operate the fluid processor. The electronic control system includes an operator interface that is connected to a programmable logic controller ("PLC"). Interfaced with the PLC are a variety of sensors used for feedback (e.g., temperature control) or the monitoring of various factors (e.g., pressure, flow rate, conductivity, endotoxin levels) in the fluid processor.

In a preferred form of the invention, the processor assembly comprises a coil-shaped heat exchanger, a reactor, and a heater wherein the reactor and heater are nested within the heat exchanger to form a compact structure. As used herein, the term "nested within the heat exchanger" means disposed or located within the volume bounded by the coil or coils of a coil-shaped heat exchanger. The heat exchanger is preferably a tube-in-tube (also called "double-pipe") type comprising an inner tube and an outer tube. An alternative heat exchanger is a shell-and-tube type comprising multiple inner tubes arranged within an outer tube or "shell". The term "annular side" refers to the annular section or space between the inner tube and the outer tube in a tube-in-tube type heat exchanger while the term "shell side" refers to the space between the inner tubes and the shell in a shell-and-tube type heat exchanger. For the sake of simplicity and unless otherwise specified, the term "circumvallate side" is used herein to refer to annular side or the shell side of a heat exchanger as the case may be, i.e. depending on which type of heat exchanger is being referred to. The term "tube side" refers to the inside section of the inner tube in a tube-in-tube heat exchanger, or the inside section of the inner tubes in a shell-and-tube heat exchanger.

As explained in more detail below, the fluid to be processed ("process fluid") is fed into the circumvallate side (i.e., the annular or shell side) of the heat exchanger. The fluid then goes into the reactor for processing by heating or cooling as the case may be. The processed fluid (i.e., "product fluid" or "product") from the reactor is fed back into the heat exchanger through the tube side. The nested configuration of the processor assembly allows the fluid processor to be compact and portable. Further, the nested configuration of the processor assembly requires only a minimum amount of energy to change the temperature of a fluid continuously flowing through the heat exchanger and reactor. The nested configuration also reduces the loss of heat to the ambient.

The preferred form of the invention further incorporates a sanitization assembly and method that allows for in situ sanitization of the fluid processor during cold start and also for in situ sanitization during shutdown so as to prevent the growth of bacteria or other micro-organisms in the fluid processor during storage. The sanitization assembly comprises an isolation valve for isolating the system from the fluid source, a drain valve, and a startup loop assembly comprising a startup flow restrictor and a four-way valve having a startup position for directing the fluid from the fluid source directly to the reactor and a normal position for directing fluid from the pump to the heat exchanger.

The method for sanitizing during startup comprises connecting the fluid processor to a suitable fluid source (e.g., tap water) having a minimum line pressure of not less than about 10 psia and not greater than about 800 psia, switching the four-way valve to its start-up position, opening the isolation valve, introducing the fluid into the fluid processor at the line pressure, switching on the heater, vaporizing the fluid as it enters the heated reactor, allowing the steam generated to go downstream from the reactor and exit at the fluid outlet, and switching the four-way valve to its normal position.

The method for sanitizing at shutdown comprises turning off the pump and heater, closing the isolation valve, allowing the residual heat of the reactor to produce steam from the residual fluid in the processor assembly to create a pressure in the processor assembly, allowing the residual fluid downstream of the processor assembly to be expelled through the fluid outlet by the steam pressure, opening the drain valve to discharge residual fluid upstream of the processor assembly, and closing the drain valve. After sanitization, the fluid processor can be stored under wet or dry conditions. The wet storage condition is achieved by attaching a container (e.g., a bag or syringe) containing a sterile solution (e.g., alcohol or SWFI) to the fluid outlet. As the fluid processor cools down a vacuum is generated within the cavities of the reactor and heat exchanger. As a result, the solution in the container is drawn into the fluid processor. By filling the cavities, the sterile solution serves as a sealant to keep the fluid processor sterile during storage. In the dry storage condition, a filter designed to prevent contaminants from passing through (e.g., a High-Efficiency Particulate Air or HEPA filter) is attached onto the fluid outlet. As the system cools, air enters the system through the filter. The bag of sterile solution or the filter is left on the fluid outlet while the fluid processor is stored away until the next use.

A specific application for the present invention is the production of SWFI by HTP. Feed water (i.e., water to be processed into SWFI) is introduced into the fluid processor and passed through the treatment assembly to remove particulate matter, oxidizable substances, dissolved gases, metals and electrolytes. The feed water then goes to the processor assembly for depyrogenation and sterilization by exposing the treated feed water to a high temperature for a prescribed amount of time. The process control system has built-in features to maintain the feed water at a sufficient pressure to prevent it from boiling, and to allow adequate retention times of the fluid in the reactor for a pre-determined operating temperature. The feed water that has been processed (i.e., SWFI) is then sent to the fluid outlet for collection.

The advantage of the present invention over the prior art is that the use of a combination of simple devices (e.g., flow restrictors, a pressure relief valve) produces a simple yet dependable process control system that obviates the need for expensive, bulky and complex sensors and valves. This allows the fluid processor to be compact but still reliable and effective. Also, the present invention allows for the continuous production of depyrogenated water rather than production by batches or semi-batches. Further, the present invention makes depyrogenation simpler and easier since HTP treatment does not leave any isolated pyrogen that would otherwise require periodic purging to remove. In addition, the present invention allows for depyrogenation at a high temperature. This results in a shorter contact time for depyrogenation and also simultaneously sterilizes the water. This eliminates the need for a separate sterilization stage such as passing water through sterilization filters. Moreover, high-temperature treatment is more reliable and effective than other approaches and is the sterilization method preferred by the FDA.

The fluid processor of the present invention is a compact, reliable, automated device having reduced energy requirements. It is designed to be easily deployable to remote locations where simplicity of operation, reliability, space, and energy requirements are critical for the continuous SWFI production from water. In addition, while the preferred embodiment of the present invention is directed to a fluid processor suitable for depyrogenation and the production of SWFI, the apparatus and method of the present invention may also find a broad range of applications in systems that have processing requirements similar to those of an SWFI fluid processor. Other objects, features, and advantages of the present invention will become apparent from the following detailed description of the best mode of practicing the invention when considered with reference to the drawings as follows:

BRIEF DESCRIPTION OF THE DRAWINGS

FIG. 6A is an exploded perspective view of another version of the processor assembly of a fluid processor embodying features of the present invention;

FIG. 6B is a top plan view of the processor assembly of FIG. 6A;

FIG. 10A is a block diagram showing the process operating conditions for cold start-up of a fluid processor embodying features of the present invention;

FIG. 10B is a block diagram showing the process operating conditions for normal operation of the fluid processor of FIG. 10A;

BEST MODE OF CARRYING OUT THE INVENTION

The apparatus and method of the present invention obtain a compact, reliable and easy to maintain and operate fluid processor having a low energy requirement that is suitable for depyrogenation and producing SWFI using HTP. A fluid processor in accordance with one embodiment of the present invention comprises a pump, a processor assembly, and a process control system comprising a flow splitter, a first and second flow restrictor, and a pressure relief valve. The process control system controls a fluid process by regulating the flow rate and pressure of the fluid within the fluid processor. Conduits (e.g., seamless tubing of stainless steel or other suitable alloys) transport the fluid between the different parts of the fluid processor. Brackets, clips or other devices commonly used in the industry hold components of the fluid processor in place.

The fluid processor is assembled from materials rated for the required temperature and pressure of the fluid process taking place in the fluid processor. The components of the fluid processor are joined together by means generally used for assembling fluid processors (e.g., welds, compression fittings). If the fluid processor is used for the production of SWFI, all components of the fluid processor must meet the sanitary standards required for SWFI production. However, it should be understood that the principles of the present invention may be used for other applications besides SWFI production and may be used to process fluids other than water or may be used to control fluid processes other than HTP.

Figure 3:
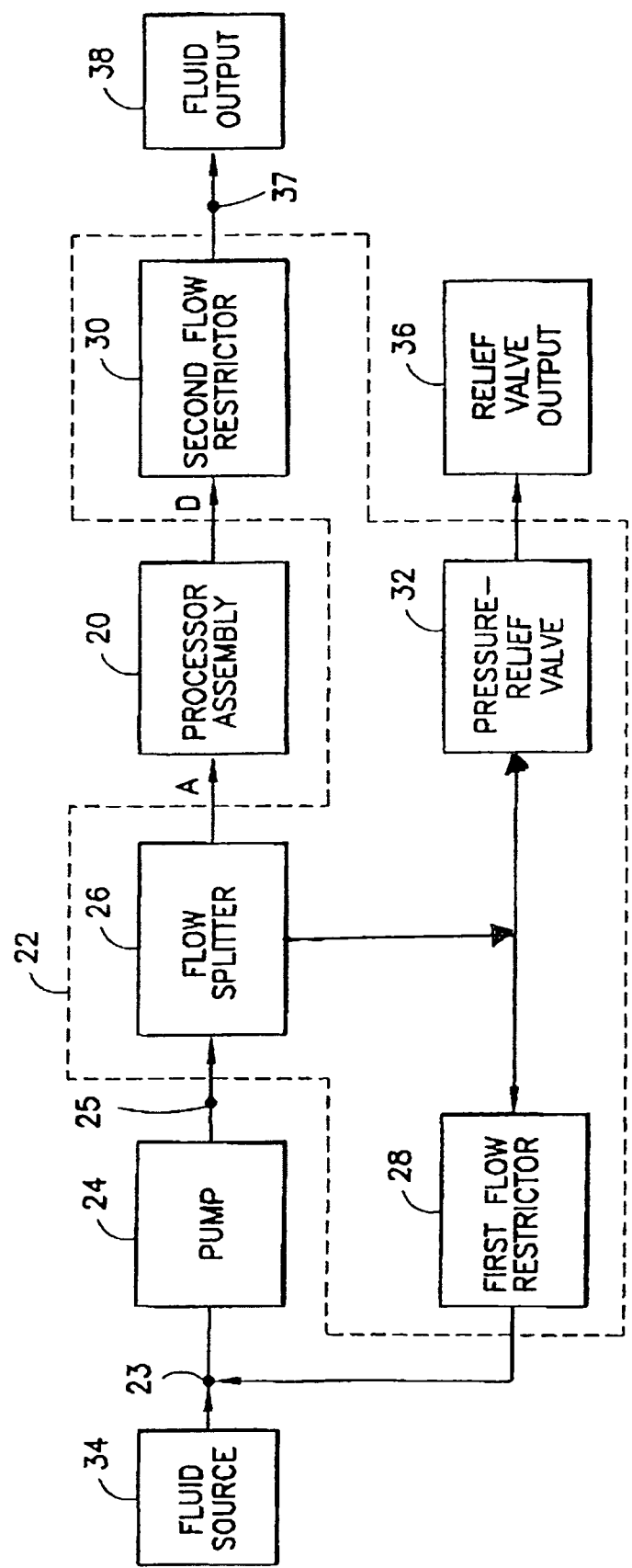
FIG. 3 is a block diagram of a fluid processor embodying features of the present invention.

Referring to FIG. 3, which illustrates a preferred embodiment of the present invention, the fluid processor generally comprises a pump 24, a processor assembly 20 and a process control system 22. The arrows show the flow of the fluid within the fluid processor. The pump 24 draws the fluid from a fluid source 34 through a fluid inlet 23 (e.g., a pump feed line), pressurizes the fluid, and send this pressurized fluid downstream towards the processor assembly 20. The pressure of the fluid source may range from about 0 psig to about 100 psig. The pump 24 raises the fluid pressure to the minimum level of the vapor pressure of the fluid that corresponds to a predetermined process temperature. The process temperature is determined according to the particular application or fluid process being performed in the fluid processor. For example, if the fluid processor is used to produce SWFI, the water must generally be heated to a temperature greater than about 180° C., preferably greater than about 250° C., to achieve rapid depyrogenation and sterilization. Once the process temperature is determined for a particular application, the vapor pressure of the fluid and the process operating pressure can be identified. The pump is selected based on the required pressures and flow rate ranges. Preferably, the pump must not introduce any foreign materials (e.g., lubricating oil) into the fluid being pressurized. Examples of pumps that meet this criterion are pumps employing diaphragms or magnetically coupled drives.

The processor assembly 20 can be any device or apparatus for processing a fluid, wherein control over the pressure, flow rate or temperature of the fluid being processed is important. The temperature of the processor assembly is controlled by heaters (e.g., electrical heaters, gas heaters) or, alternatively, coolers (e.g., chillers). The processor assembly may use multiple thermocouples as sensors for temperature feedback.

As shown in FIG. 3, the process control system 22 comprises a flow splitter 26, a first flow restrictor 28, a second flow restrictor 30 and a pressure relief valve 32. The flow splitter 26 is positioned downstream of the pump 24 and diverts a portion of the fluid from the pump towards the first flow restrictor 28. The first flow restrictor 28, in turn, sends the diverted fluid back to the fluid inlet 23. The foregoing diversion of a portion of the fluid coming from the pump forms a recirculating loop that controls the flow rate of the fluid in the fluid processor. Preferably, the flow splitter is a RO or cross-flow ultra/micro filtration device because these devices offer benefits not provided by an ordinary flow splitter. An RO device typically operates at about a 70% rejection ratio. This means that only about 30% of the incoming fluid or feed stream is allowed to pass the membrane as filtrate, while about 70% of the incoming fluid is rejected as retentate. Since the performance of RO or cross-flow ultra/micro filtration devices is enhanced by increasing the shear rate of fluid at the surface of the membrane or filter, it is desirable to maintain a high fluid flow rate. Recirculating the reject stream (i.e., the retentate) back into the fluid processor inlet 23 achieves a flow rate in the RO or cross-flow ultra/micro filtration device much higher than it would be without the recirculation loop. Another benefit of recirculating the reject stream is that as the fluid passes through the pump head (not shown), the temperature of the fluid rises due to friction forces and a higher fluid temperature improves the performance of the RO membranes.

Alternatively, evaporators (not shown) may be used as a flow splitter. In this embodiment, the pressurized fluid coming out of the pump is heated. As the heated fluid enters the evaporators, the pressure of the fluid is reduced so as to flash evaporate a portion of the fluid. The vapor fraction continues downstream to the processor assembly while the liquid fraction is cooled and recirculated back into the fluid processor inlet.

The pressure relief valve 32 is interposed between the flow splitter 26 and the first flow restrictor 28. The pressure relief valve is designed to open when the pressure of the fluid in the recirculating loop reaches a specified pressure and to close when the fluid pressure falls below the specified pressure. Preferably, the pressure relief valve is an adjustable spring-loaded type pressure relief valve. When the pressure relief valve 32 is open, fluid from the recirculating loop is diverted to a relief valve output 36 via a relief valve drain (not shown). The pressure-relief valve 32 is initially adjusted (i.e., "tuned") to the specified fluid pressure. Once the pressure-relief valve is tuned and the pressure-relief valve stem (not shown) is locked, no further operator interaction is needed during normal operation of the fluid processor.

The second flow restrictor 30 is located downstream of the processor assembly 20. The function of the second flow restrictor 30 is to maintain a backpressure within the fluid processor. As the term is used herein, a "flow restrictor" is a conduit with a sudden or gradual change in its internal diameter such that the fluid flow through the conduit is restricted. Each of the two flow restrictors 28 and 30 is designed so that their length and internal diameter create a pressure differential. This pressure differential is based on a specified fluid flow rate and viscosity, which, in turn, depend on the particular fluid process being performed in the fluid processor. Both or either of the flow restrictors may have fixed or adjustable settings. Examples of suitable flow restrictors are fixed length capillary tubes, adjustable regulating valves, and metering valves.

Figure 11A:
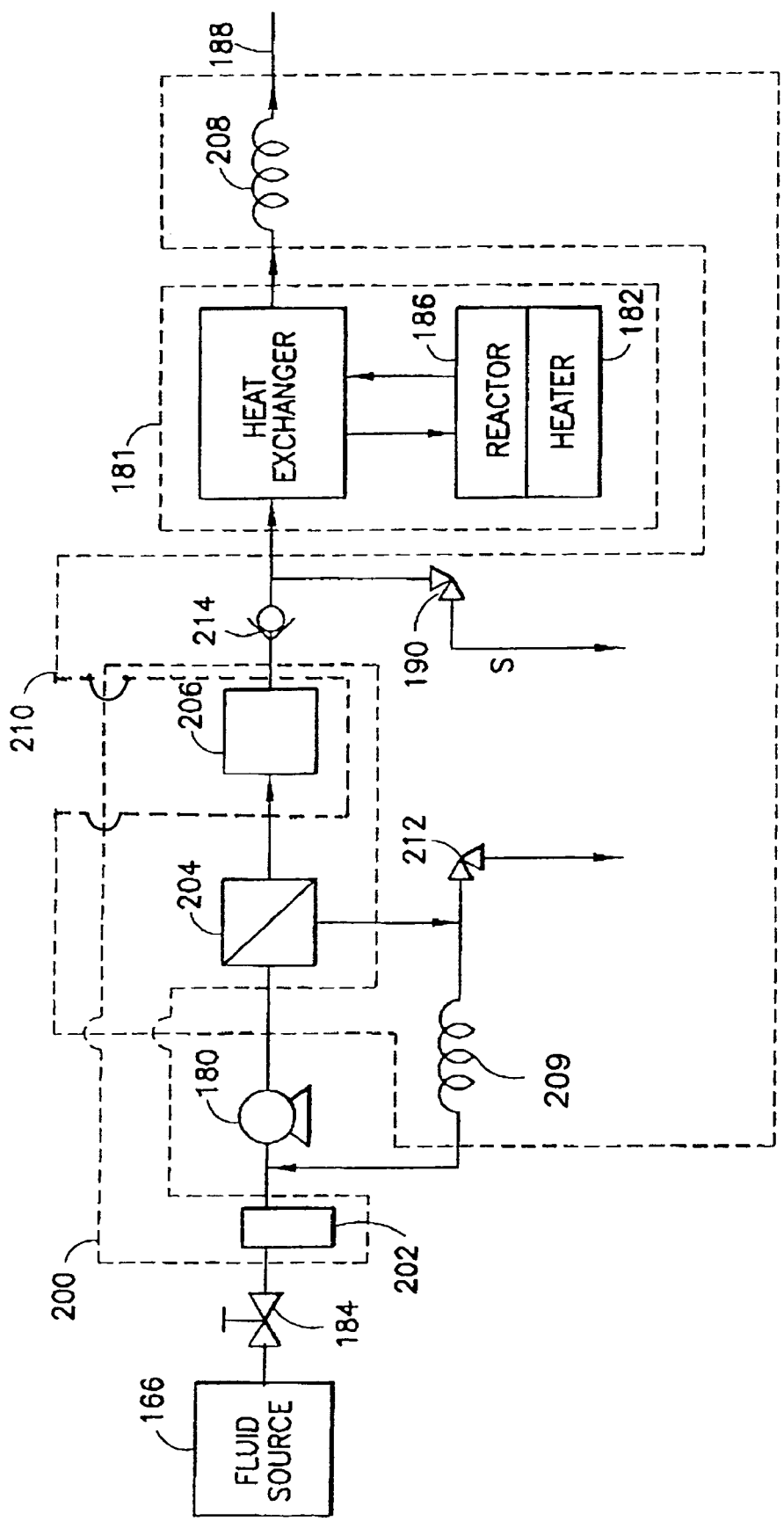
FIG. 11A is a block diagram showing the process operating conditions for shutdown of a fluid processor embodying features of the present invention.

Referring to FIG. 3, when the fluid processor is in operation, the pump 24 draws fluid from the fluid source 34 via the fluid inlet 23, pressurizes the fluid and sends it downstream to the processor assembly 20 for processing. The fluid that has been processed by the processor assembly 20 (i.e., product fluid) is then sent downstream to a fluid output 38 for collection. The process control system 22 controls the pressure and flow rate of the fluid being processed at various locations in the fluid processor, primarily the pressure and flow rate of the fluid at a pump outlet 25, the processor assembly 20, and a fluid outlet 37. The pressure and flow rate of the fluid at the pump outlet 25 are controlled by the combination of the flow splitter 26, the first flow restrictor 28, and the pressure relief valve 32. The fluid pressure and flow rate within the processor assembly 20 and at the fluid processor outlet 37 are functions of the pump outlet 25 and the settings of the pressure relief valve 32, flow splitter 26, and flow restrictors 28 and 30. Referring to FIG. 11A, a check valve 214 may be positioned immediately upstream of a processor assembly 181. The purpose of the check valve is to prevent fluid from flowing back upstream. Additional check valves may also be positioned at other locations for preventing the fluid from flowing back upstream.

Figure 1:
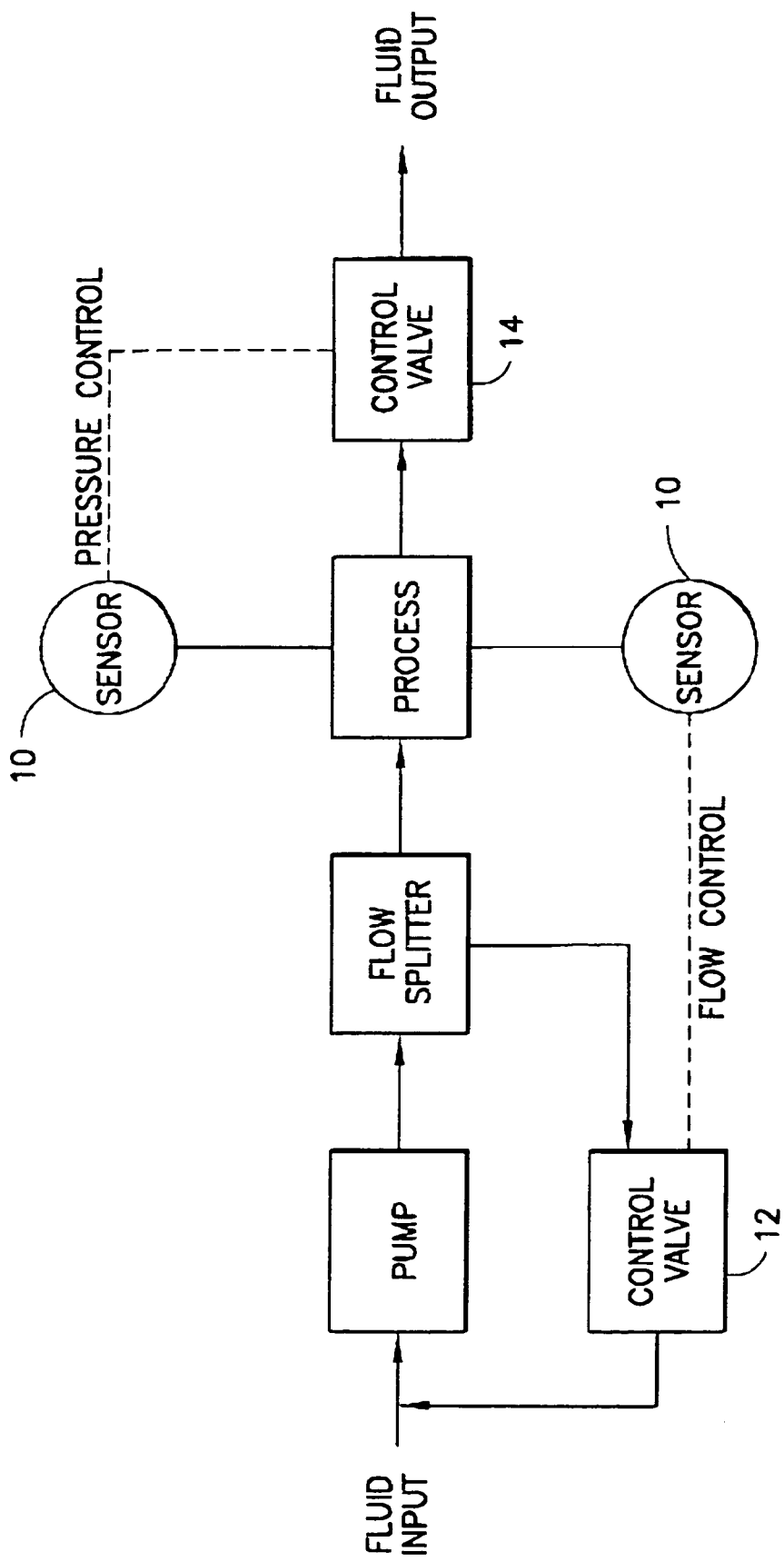
FIG. 1 is a block diagram of a complex process control system of the prior art.
Figure 2:
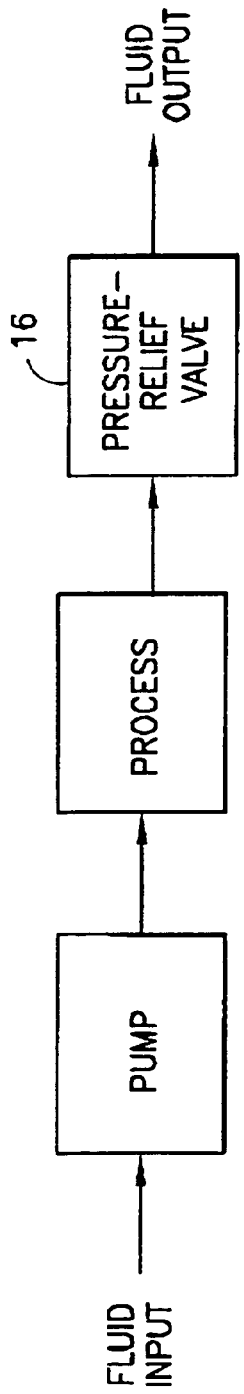
FIG. 2 is a block diagram of a simple process control system of the prior art.

Unlike complex process control systems of the prior art (see, e.g., FIG. 1), no flow rate or pressure sensors are used for feedback control. Of course, although it is not required by the present invention, flow rate or pressure sensors may be used for process monitoring and quality assurance purposes. A further advantage of the present invention over the prior art is that the use of the combination of simple devices (e.g., a flow splitter, flow restrictors) makes the process control system of the present invention more reliable and effective compared to simple process control systems of the prior art (see, e.g., FIG. 2).

In one embodiment of the present invention (see, FIGS. 3 and 4), the processor assembly comprises a heat exchanger 40, a reactor 42 and a heater 46. Generally, any heat exchanger suitable for use in a fluid processor may be used. However, if the fluid processor is to be used for producing SWFI, the heat exchanger must be of a type recommended by FDA as suitable for use in SWFI production, e.g., double-tubesheet, tube-in-tube, and shell-and-tube type heat exchangers. As discussed in more detail below, the heat exchanger recovers thermal energy by exchanging heat between a process fluid and a product fluid.

The heater 46 can be any type of heater suitable for use in a fluid processor. Examples of suitable heaters are electric heaters, gas-fired heaters, or hot gases or fluids generated from an external source such as the exhaust of a combustion process or a hot fluid stream. The selection of which particular heater to use depends on availability and the requirements of the particular fluid process taking place in the fluid processor. The heater 46 heats the reactor 42. The reactor, in turn, heats the fluid flowing through the reactor 42. The temperature of the fluid is controlled by the heater 46, which, in turn, may be controlled by a simple temperature controller (not shown). Multiple thermocouples (not shown) may be used as sensors to monitor temperature.

In operation, (see, FIGS. 3 and 4) the process fluid is introduced into the circumvallate side of the heat exchanger 40 (see, arrow A) where it is pre-heated by the product fluid flowing in the opposite direction (i.e., counter-currently) through the tube side of the heat exchanger (see below). After passing through the circumvallate side of the heat exchanger 40, the process fluid enters the reactor 42 (see, arrow B) where it is heated by the heater 46 to the required temperature for processing (i.e., the "processing temperature" or "process temperature"). The processed fluid (i.e., "product fluid") exits from the reactor (see, arrow C) and enters the tube side of the heat exchanger 40 to be cooled by the process fluid flowing though the circumvallate side. The product fluid then goes through the second flow restrictor (see, arrow D) and exits the fluid processor at the fluid outlet 37.

Figure 5A:
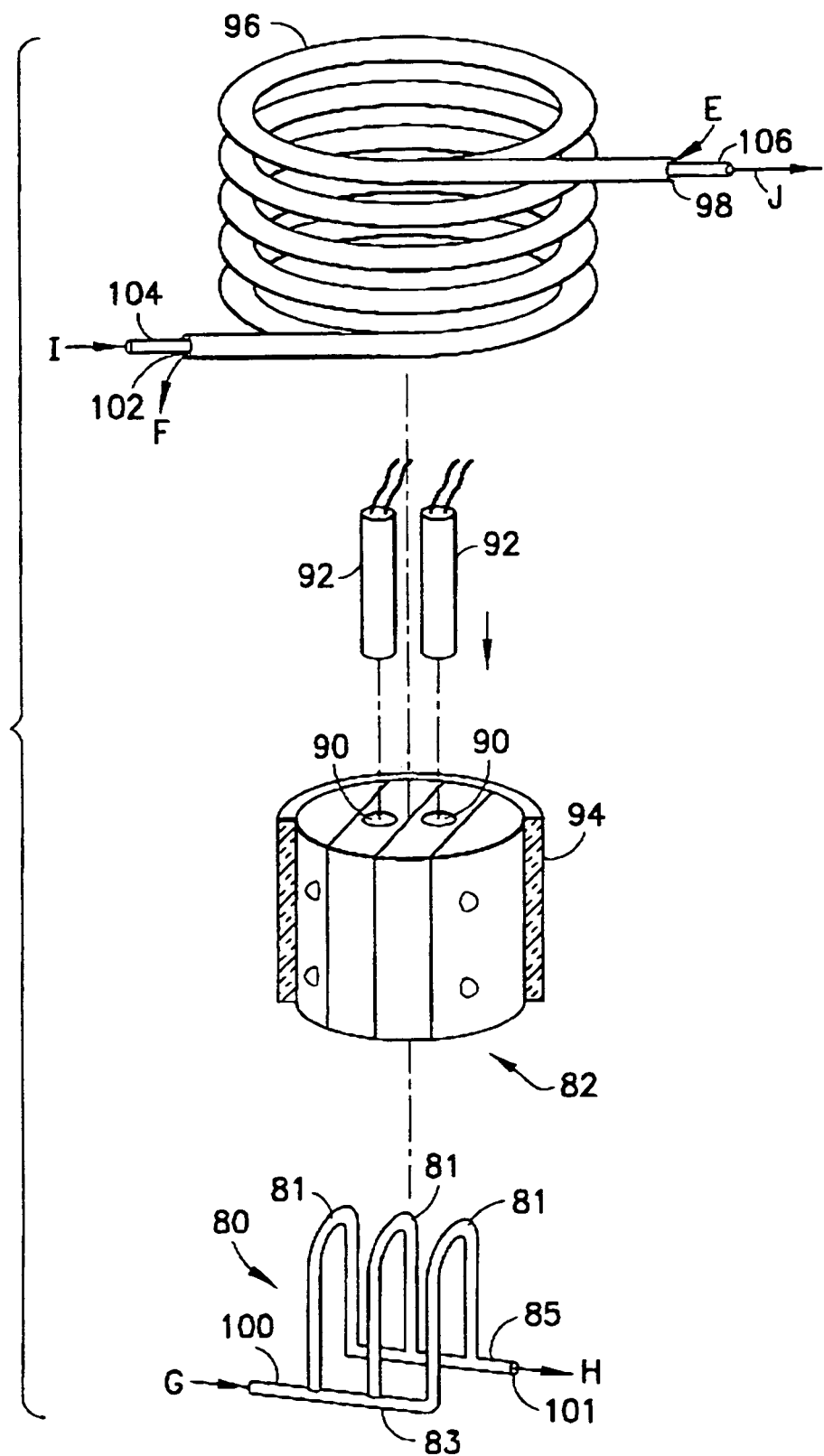
FIG. 5A is an exploded perspective view of the processor assembly of a fluid processor embodying features of the present invention.

In a preferred embodiment of the present invention the processor assembly is a compact unit comprising a helical coil tube-in-tube heat exchanger wherein the reactor and heater (or, alternatively, a cooler) arranged in a nested configuration similar to that of a Russian "matryoshka" doll within the heat exchanger. Preferably, the reactor and the heat exchanger are contained in a temperature homogenizer. One version of the processor assembly of a preferred embodiment of the present invention is shown in FIG. 5A. In FIG. 5A, a reactor 80 and heaters 92 are contained within a temperature homogenizer 82. The temperature homogenizer 82 is, in turn, nested within a helical coil, tube-in-tube type heat exchanger 96.

The reactor 80 comprises a series of hollow U-shaped reactor tubes 81. The number of reactor tubes is determined by fluid flow rate and reactor volume requirements. Generally, increasing the number of reactor tubes results in an increased surface area available for heat transfer. One end of each reactor tube 81 is connected to a hollow feed tube 83. The feed tube 83 is closed at one end and has an inlet 100 at the other end. The other end of each reactor tube 81 is connected to a hollow product tube 85. The product tube is closed at one end and has an outlet 101 at the other end. The reactor tubes 81, inlet tube 100 and product tube 101 are fabricated using well-known methods in the industry (e.g., welding, casting) from materials that can hold the internal fluid pressure, have relatively high thermal conductivity, and which display high corrosion resistance to the process fluid and product fluid under high temperature and high pressure. A stainless steel or equivalent alloy of nickel, chromium, and iron is preferred.

Figure 5B:
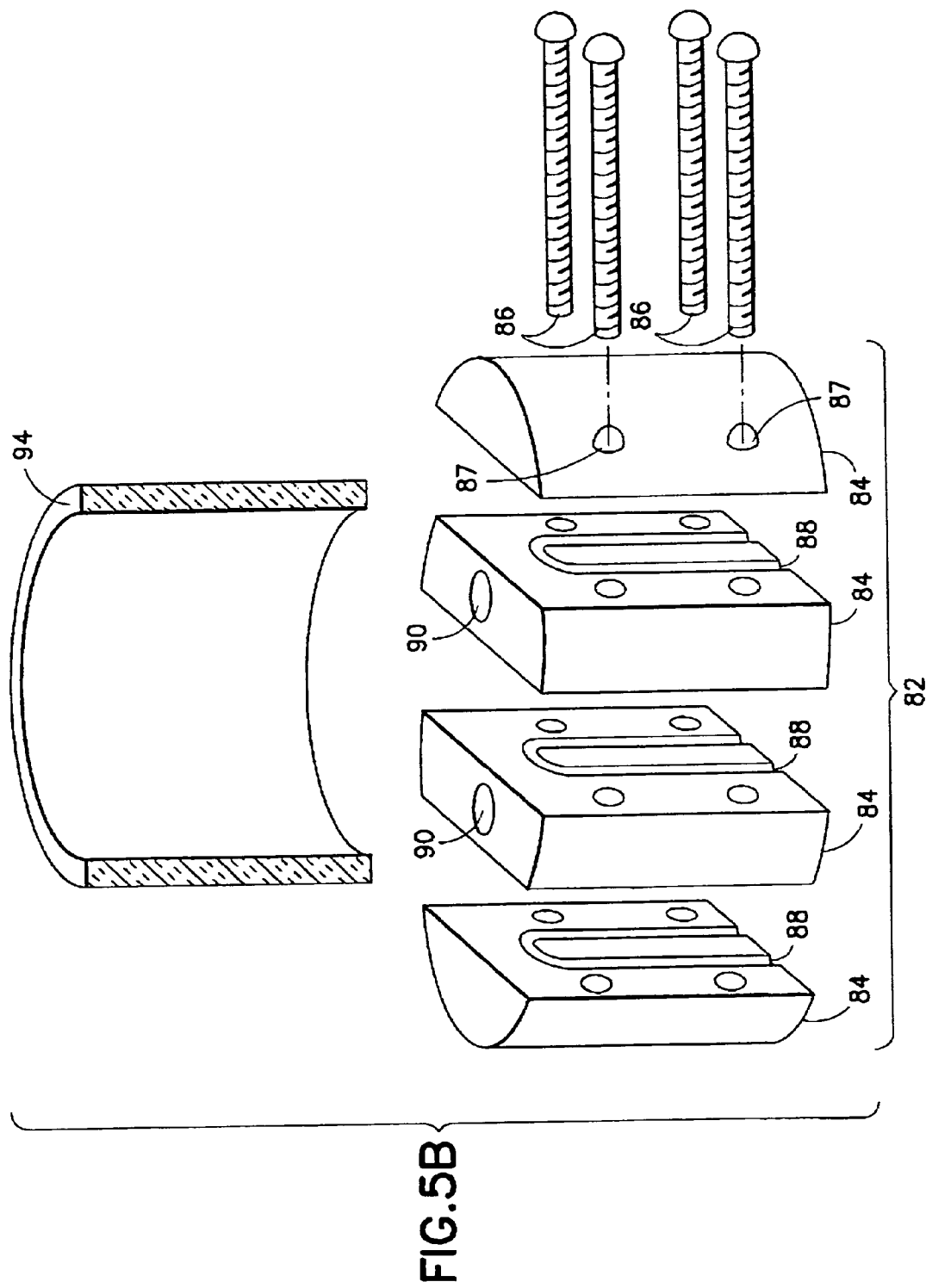
FIG. 5B is an exploded perspective view of a temperature homogenizer for use with the processor assembly of FIG. 5A.

As shown in FIGS. 5A and 5B, the temperature homogenizer 82 is "dimensioned" (i.e., sized, shaped, constructed, and adapted) to enclose the heaters 92 and reactor 80 and to allow the temperature homogenizer 82 to be nested within the heat exchanger 96. The purpose of the temperature homogenizer 82 is to maximize the heat transfer to the reactor by providing more well-contacted surfaces for heat transfer. At the same time, the temperature homogenizer 82 also maximizes the stability of the temperature of the fluid within the reactor by acting as form of "thermal capacitor", i.e., it protects the reactor 80 from the effects of sudden heating or cooling. The temperature homogenizer 82 shown in FIGS. 5A and 5B is in the shape of a right circular cylinder. However, other suitable shapes may be used (e.g., obround or oval shapes) without departing from the spirit of the present invention.

The temperature homogenizer 82 consists of a multiplicity of blocks 84 made of a metal having high thermal conductivity, preferably copper, brass, or silver. The blocks 84 have reactor cavities 88 to contain the reactor 80 and also heater cavities 90 to hold the heaters 92. The blocks 84 are held together by fasteners 86 (e.g., screws) passing through fastener holes 87 in the blocks. The blocks 84 can be formed by machining or casting a suitable metal. The number of blocks 84 forming the temperature homogenizer 82 depends on the number of reactor tubes 82 and the degree of need for ease of assembly and disassembly. Constructing the temperature homogenizer 82 from blocks 84 makes it easy to replace the reactor 84 by removing the fasteners 86 holding the blocks 84 together. The heaters 92 are inserted into heater holes 90. In FIG. 5A, electrical cartridge heaters 92 are shown. However, other suitable heaters may be used without departing from the spirit of this invention. Preferably, a multiplicity of heaters is used because increasing the number of heaters results in better temperature distribution in the temperature homogenizer. In an alternative embodiment (not shown), the temperature homogenizer may be cast as a single unitary structure with the reactor formed directly into the temperature homogenizer itself rather being a separate structure. When assembling together the reactor 80, heaters 92 and temperature homogenizer 82, a high-temperature thermally conductive sealing material (e.g., powdered silver or copper formulated in a paste form) may be applied to the contact surfaces for improved heat transfer.

The temperature homogenizer 82 is enclosed by a jacket 94. Preferably, the jacket completely covers the temperature homogenizer. In FIGS. 5A and 5B the top and bottom of the insulating jacket 94 has been cut away to provide a better view of the temperature homogenizer 82. The jacket 94 is made of an insulating material suitable for the temperatures that will be produced when the fluid processor is operating. Such materials are commercially available on the open market. The purpose of the jacket 94 is to minimize the heat lost to the ambient. As used herein, the term "ambient" refers to the air surrounding the processor assembly.

In operation (see, FIG. 5A), the process fluid enters the annular side of the heat exchanger 96 (see, arrow E) at an annular side inlet 98 and is pre-heated by the product fluid flowing through the tube side of the heat exchanger 96. The pre-heated process fluid exits the heat exchanger at an annular side outlet 102 (see, arrow F) and is fed through a reactor inlet 100 (see arrow G) into the reactor 80. The process fluid is heated in the reactor 80 to the process temperature by the heaters 92. The processed fluid or product exits the reactor 80 at a reactor outlet 101 (see, arrow H) and is fed through a tube side inlet 104 into the tube side (see, arrow I) of the heat exchanger 96 where it is cooled by the process fluid flowing through the annular side. The product fluid then exits the heat exchanger at a tube side outlet 106 (see, arrow J).

Alternatively, the processor assembly of FIG. 5A may use coolers (not shown) instead of the heaters 92 in a situation wherein the fluid process requires cooling the fluid. In this case, coolers instead of heaters are placed in the heater cavities 90. In this embodiment the process fluid is pre-cooled as it passes through the heat exchanger 96 instead of being pre-heated. Also, in this embodiment, the temperature homogenizer 82 maximizes the heat transfer to the cooler from the reactor and maximizes the stability temperature of the fluid using the same mechanism described above.

Instead of the single heat exchanger 96, another version of the processor assembly of FIG. 5A uses a heat exchanger assembly comprised of two or more helical coil tube-in tube heat exchangers stacked vertically on top of one another. See, FIGS. 5C and 5D. The heat exchangers may be connected together in series (see, FIG. 5C) or in parallel (see, FIG. 5D) or a combination thereof. However, the processor assemblies of FIGS. 5C and 5C still use the same reactor 80 and heaters 92 contained within the temperature homogenizer 82 as that of the processor assembly of FIG. 5A. The actual number of the heat exchangers in the stack is determined by the height of each heat exchanger and the height of the reactor 80, heaters 92 and temperature homogenizer 82.

Figure 5C:
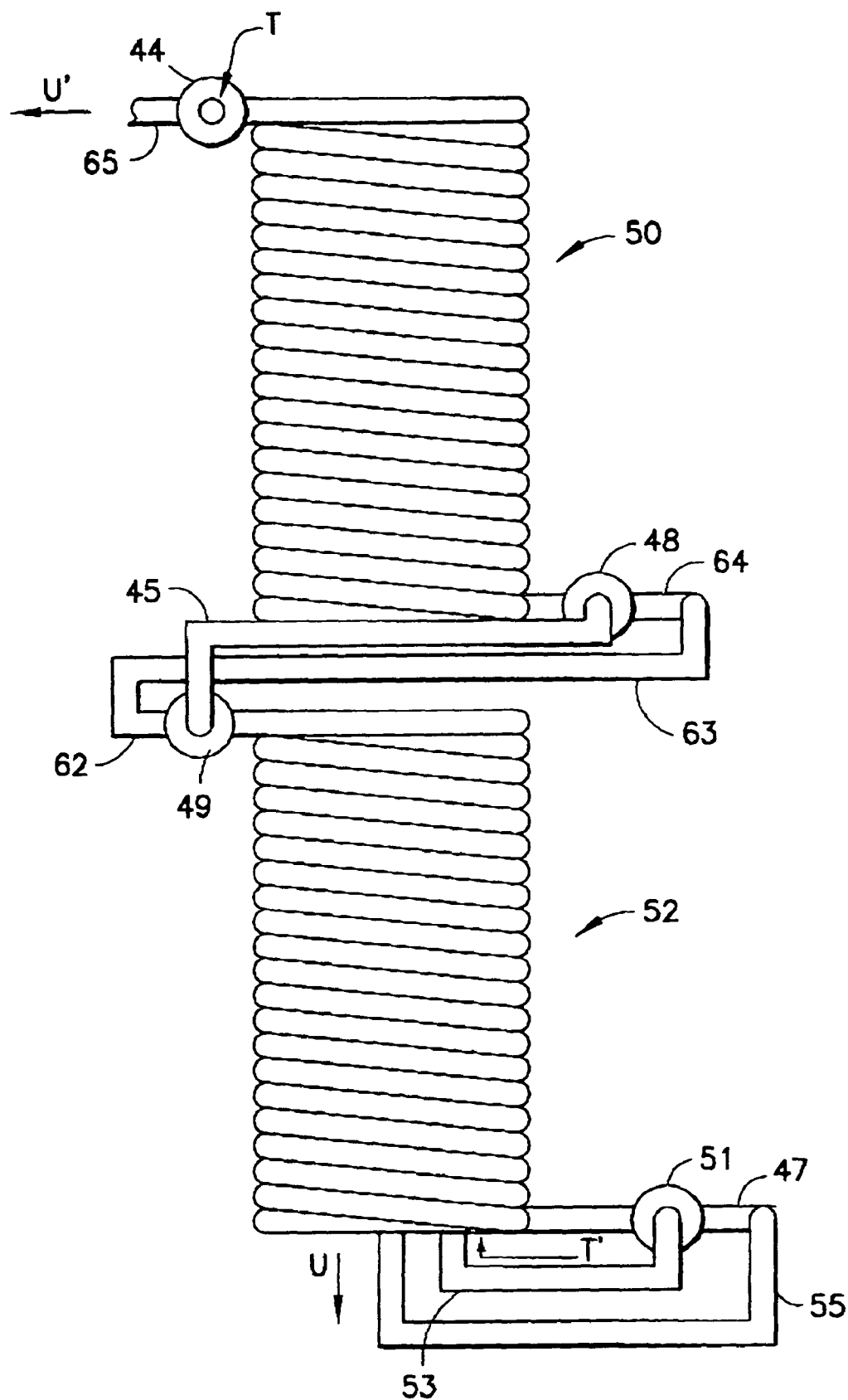
FIG. 5C is a plan view of a heat exchanger assembly for use with the processor assembly of FIG. 5A.

Referring to FIG. 5C, the heat exchanger assembly comprises a top heat exchanger 50, and a bottom heat exchanger 52 that are connected together in series. Both heat exchangers are helical coil, tube-in-tube heat exchangers. The heater, reactor and temperature homogenizer (not shown) are nested within the second heat exchanger 52 in the same manner as described above with respect to the heat exchanger 96 of FIG. 5A. In operation, the process fluid enters an annular side inlet 44 (see, arrow T) of the top heat exchanger 50 where it is pre-heated by the product fluid counter-currently flowing through the tube side. The process fluid exits via an annular side outlet 48 and is carried by a first annular outlet conduit 45 to an annular side inlet 49 of the bottom heat exchanger 52. The process fluid flows through the annular side of the bottom heat exchanger 52 where it is further pre-heated by the product fluid counter-currently flowing through the tube side. The process fluid exits the bottom heat exchanger 52 via an annular side outlet 51 and is carrier by a second annular outlet conduit 53 (see arrow T') into the reactor (not shown) where is heated to the process temperature by the heater (not shown). The processed fluid or product exits the reactor and is carried by a first tube inlet conduit 55 to a tube side inlet 47 (see arrow U) of the bottom heat exchanger 52. The product flows up the tube side of the bottom heat exchanger wherein it is cooled by the process fluid counter-currently flowing through the annular side. The product exits the bottom heat exchanger at a tube side outlet 62 and is carried by a second tube inlet conduit 63 to a tube side inlet 64 of the top heat exchanger 50. The product moves through the tube side of the top heat exchanger 50 wherein it is further cooled by the process fluid counter-currently flowing through the annular side. The product exits the top heat exchanger 50 at a tube side outlet 65 (see arrow U').

Figure 5D:
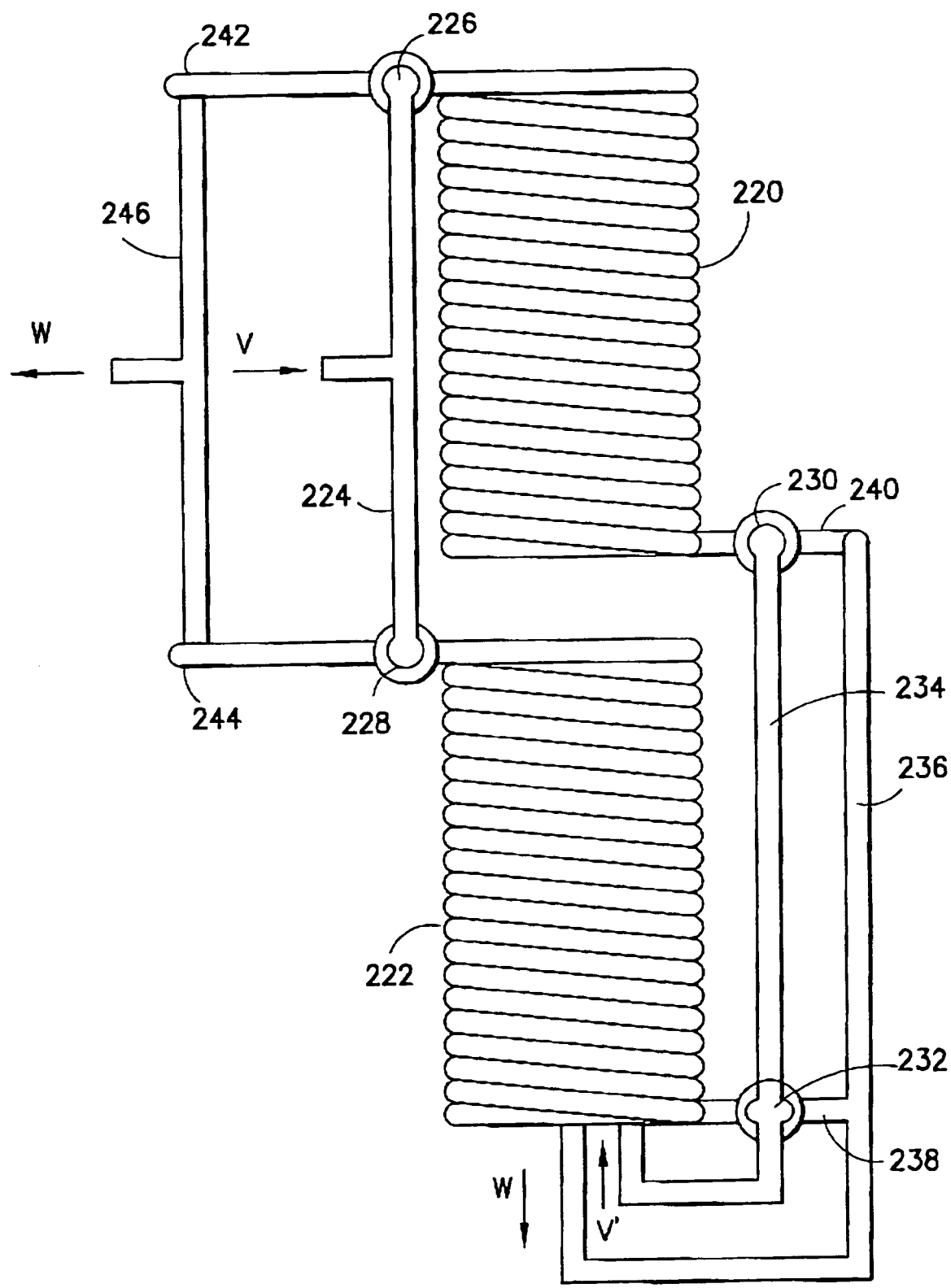
FIG. 5D is plan view of another version of the heat exchanger assembly for use with the processor assembly of FIG. 5A.

Referring to FIG. 5D, the heat exchanger assembly comprises an upper heat exchanger 220 and a lower heat exchanger 222. Both heat exchangers are helical coil, tube-in-tube heat exchangers that are connected together in parallel. The heater, reactor and temperature homogenizer (not shown) are nested within the upper heat exchanger 220 in the same manner as described above with respect to the heat exchanger 96 of FIG. 5. Alternatively the heater, reactor and temperature homogenizer may be nested with lower heat exchanger 222, or nested between both the upper heat exchanger 220 and lower heat exchanger 222. In operation, the process fluid is introduced into the annular sides of heat exchangers 220 and 222 (see, arrow V) through an annular inlet conduit 224 that is connected to annular side inlets 226 and 226 of heat exchangers 220 and 222 respectively. The process fluid is pre-heated by the product fluid counter currently flowing through the tube sides of heat exchangers 220 and 222. The pre-heated process fluid exits the heat exchangers through annular side outlets 230 and 232 of heat exchangers 220 and 222 respectively. An annular outlet conduit 234 that is connected to annular side outlets 230 and 232 of heat exchangers 220 and 222 respectively carries the pre-heated process fluid (see, arrow V') to the reactor (not shown) where it is heated to the process temperature. The product fluid exits the reactor (see, arrow W) and is introduced into the tube sides of both heat exchangers through a tube inlet conduit 236 that is connected to tube side inlets 238 and 240 of heat exchangers 220 and 222 respectively. The product fluid is cooled by the process fluid counter-currently flowing through the annular sides of the heat exchangers. The cooled product fluid exits both heat exchangers (see arrow W') through a tube outlet conduit 246 that is connected to tube side outlets 242 and 244 of heat exchangers 220 and 222 respectively.

Another version of the processor assembly of a fluid processor embodying features of the present invention is shown in FIG. 6A. In this version, the processor assembly comprises a heater 62 shaped in the form of a hollow tube, a rod-shaped reactor 60, and a multiplicity of tube-in-tube type heat exchangers 61 shaped in the form of "rug rope coils". The reactor 60 is inserted into the heater 62. The heater 62, in turn, is nested within the hollow space bounded by the coils of heat exchangers 61 which are stacked vertically on top of one another.

The reactor 62 is fabricated using well-known methods in the industry (e.g. welding, casting) from materials that can hold the internal fluid pressure, have relatively high thermal conductivity, and which display high corrosion resistance to the process fluid under high temperature and high pressure. A stainless steel or equivalent alloy of nickel, chromium, and iron is preferred. The heater 62 is selected from commercially available cable heaters or band heaters. The reactor 60 is inserted into the heater 62 to form a reactor-heater assembly 66. The reactor-heater assembly 66, in turn, is nested within the stacked heat exchangers 61 (see, FIG. 6B). The number of the heat exchangers 61 in the stack is determined by the diameter of the outer tubes of the heat exchangers 61 and the height of the reactor-heater assembly 66. The heat exchangers 61 may be connected to each other either in parallel, in series or a combination of both as described earlier above with respect to the heat exchanger assemblies of FIGS. 5C and 5D.

Figure 7:
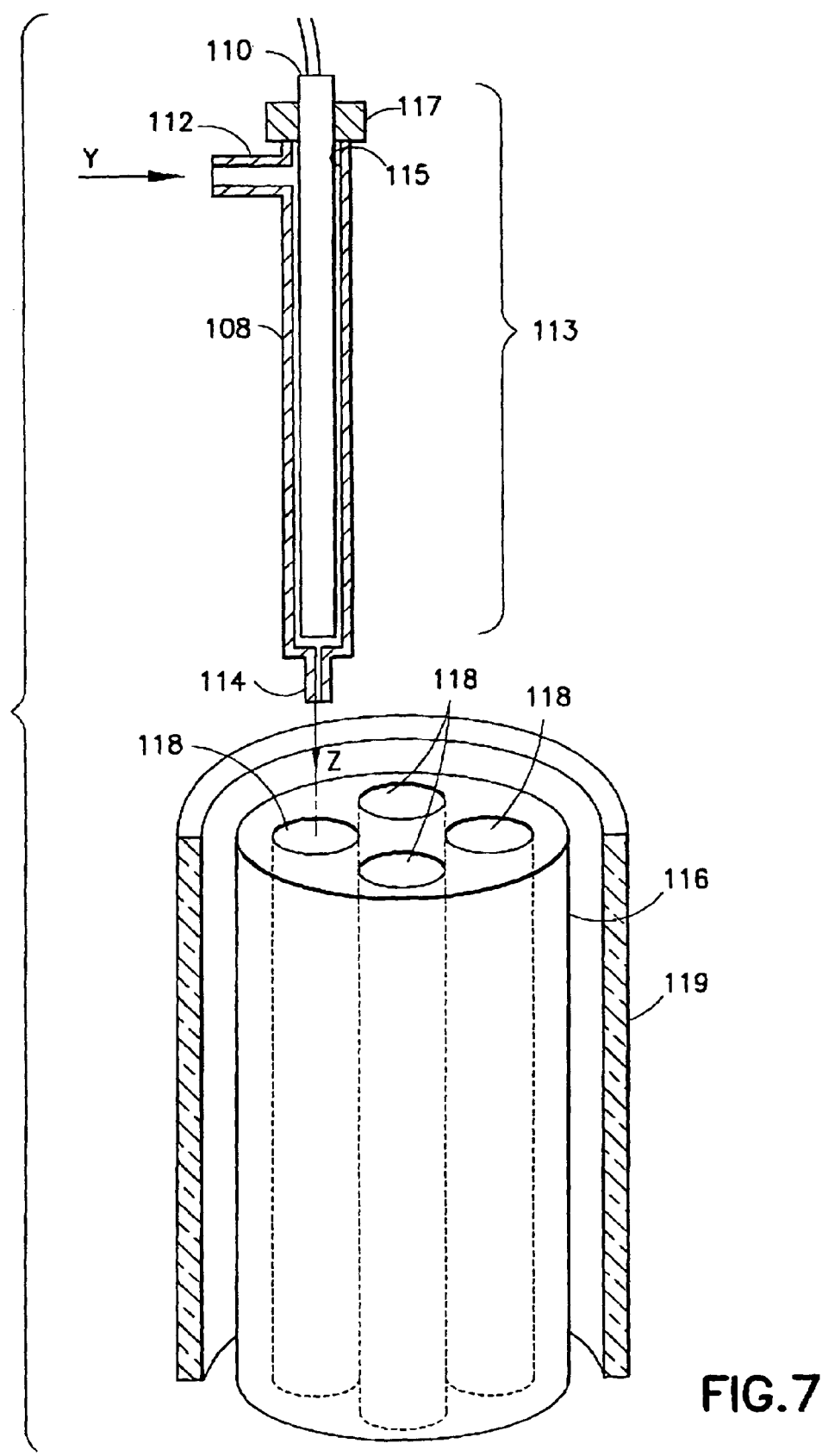
FIG. 7 is an exploded perspective view of a heater-reactor assembly for use with the processor assembly of FIG. 6A.

FIG. 7 shows another version of the reactor-heater assembly and the temperature homogenizer for use with the processor assembly of FIGS. 5A and 6A. In FIG. 7, the reactor-heater assembly 113 comprises a reactor 108 in the form of a hollow tube having an inlet 112, an outlet 114 and a heater opening 115. The reactor 108 is fabricated in the same manner as the reactors previously described above. To form the reactor-heater assembly 113, a cartridge type electrical heater 110 is inserted into the heater opening 115 of the reactor 108 and is locked and sealed into place with a compression fitting 117.

The temperature homogenizer 116 is cast or machined from the same materials previously described above and is dimensioned to allow the temperature homogenizer 116 to be nested within the coils of a coil-shaped heat exchanger. The temperature homogenizer 116 is formed in the shape of a right circular cylinder. However, as stated previously above, other suitable shapes may be used without departing from the spirit of the present invention. A multiplicity of cavities 118 extend through the temperature homogenizer. These cavities 118 are for holding the reactor-heater assemblies 113 within the temperature homogenizer. A jacket 119 of insulating material surrounds the sides temperature homogenizer 116. The jacket is made from a material suitable for the temperatures that will be produced when the fluid processor is operating. Such materials are commercially available on the open market.

The reactor-heater assembly 113 is inserted into the cavity 118 so that the outlet 114 protrudes from the bottom of the temperature homogenizer 116 and the inlet 112 protrudes from the top of the temperature homogenizer. A multiplicity of reactor-heater assemblies 113 is contained within the temperature homogenizer 116. However, for simplicity, only one reactor-heater assembly is shown in FIG. 7. The number of reactor-heater assemblies used depends on the overall size of the temperature homogenizer, the diameter of the reactor 108, and the diameter of the heater 110. The process fluid enters the reactor 108 through the inlet 112 (see, arrow Y) and is heated by the heater 110 to the process temperature. The product exits the reactor 108 through the outlet 114 (see, arrow Z).

Figure 8A:
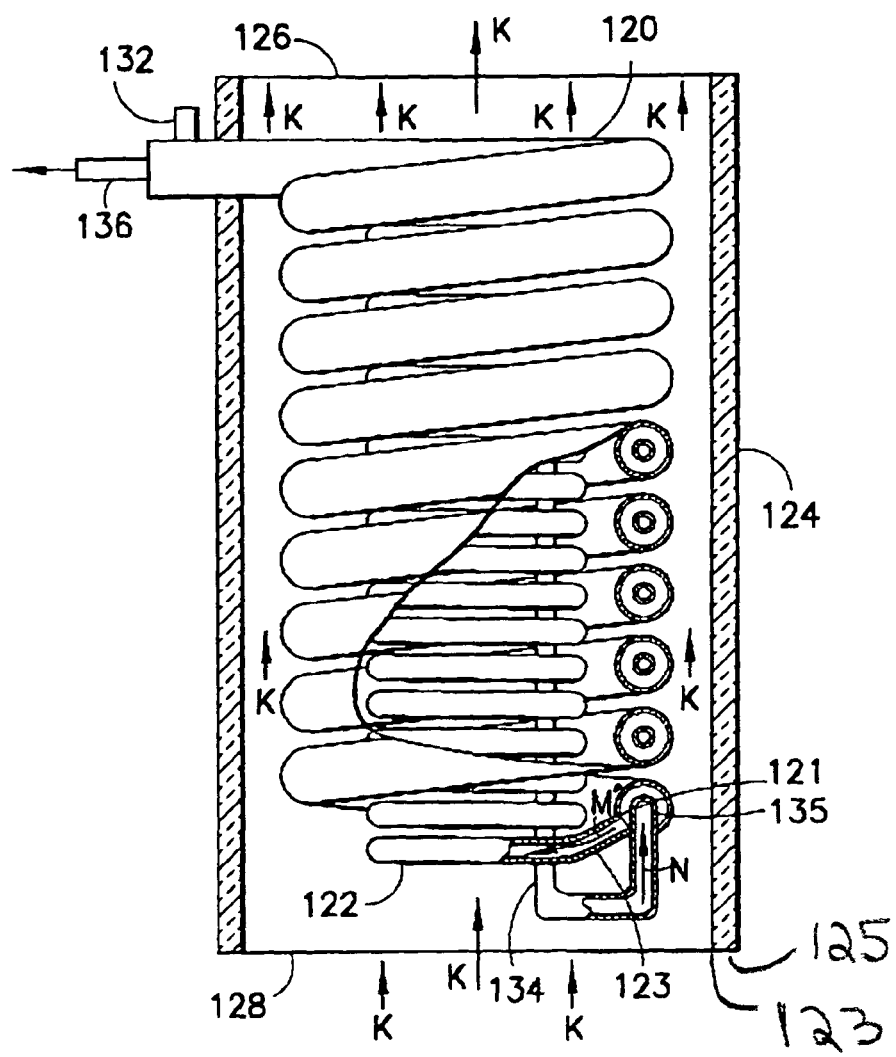
FIG. 8A is a partial sectional plan side view of another version of the processor assembly of a fluid processor embodying features of the present invention.
Figure 8B:
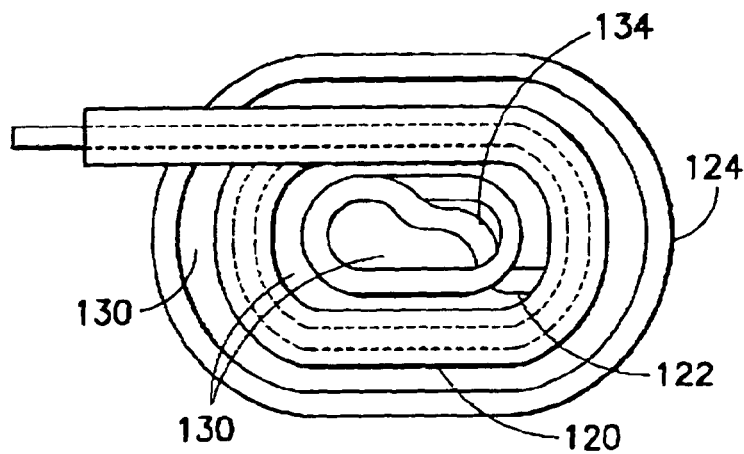
FIG. 8B is a top view of the processor assembly of FIG. 8A.

Another version of the processor assembly of a fluid processor embodying features of the present invention is shown in FIG. 8A. In this arrangement, the processor assembly comprises a gas-fire heater (not shown), a helical coil, tube-in-tube heat exchanger 120, a helical coil-shaped hollow tube reactor 122 and an insulated duct 124. The reactor 122 is fabricated in the same manner as the reactors discussed above and is dimensioned to allow it to be nested within the heat exchanger 120 but leaving sufficient space to allow for air passages 130 and room for the reactor 122 and heat exchanger 120 to expand. See, FIG. 8B. The insulated duct 124 is made from an insulating material suitable for use with the temperatures encountered when the fluid processor is in operation. Such materials are commercially available on the open market. Preferably, the duct 124 comprises a support structure 123 fabricated from materials resistant to high temperature oxidizing environments such as nickel, chromium, or iron alloys, or ceramic materials. The structure 123, in turn, is covered by one or more layers 125 of the insulating material. The duct 124 has a vent 126 at the top and a hot gas inlet 128 at the bottom. Further, the duct 124 is dimensioned to allow it to completely enclose the coils of the heat exchanger 120 but still leave enough space to allow for air passages 130 and also room to allow expansion of the heat exchanger 120. See, FIG. 8B.

Figure 8C:
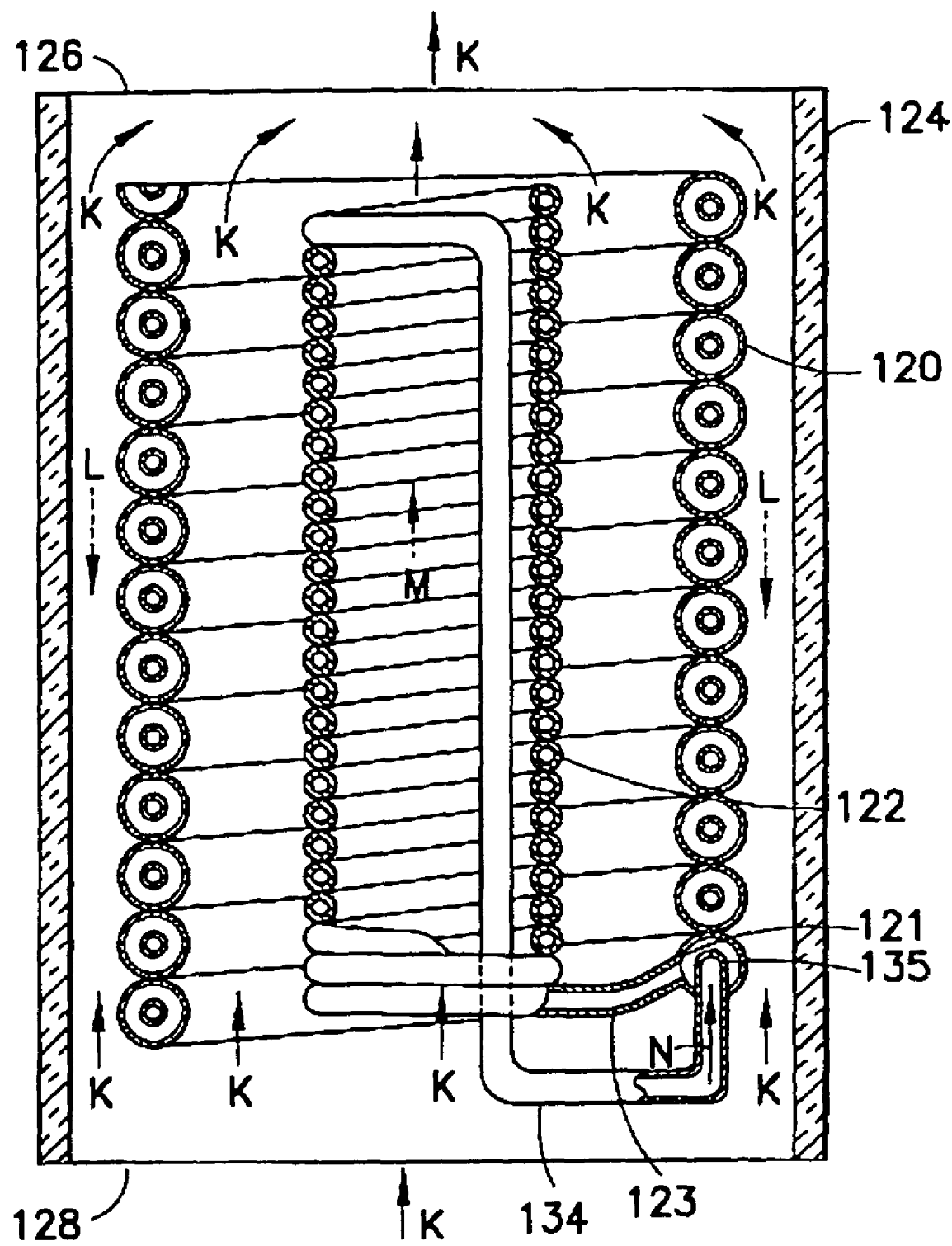
FIG. 8C is a sectional side plan view of the processor assembly of FIG. 8A.

The reactor 122 is nested within the heat exchanger 120. The heat exchanger 120 is, in turn, disposed within the insulated duct 124. In operation (see, FIGS. 8B and 8C), a high-temperature gas stream (arrow K) produced by the gas-fire heater (not shown), or alternatively, some other external heat source, enters the duct 124 through the hot gas inlet 128 and moves upwards to the vent 126 through the air passages 130. As shown in FIG. 8C, as the gas stream (arrow K) goes up the air passages 130, it moves counter-currently with the process fluid flow (arrow L) in the annular section of the heat exchanger 120 and co-currently with the product fluid flow (arrow M) in the reactor 122. The counter-current flow of the process fluid (arrow L) with respect to that of the gas stream (arrow K) makes the heat exchange more efficient as compared to co-current flow. The co-current flow of the product fluid (arrow M) with respect to that of the gas stream (arrow K) raises the fluid temperature in the reactor as quickly as possible and maintains the temperature relatively constant along the reactor length.

The process fluid is introduced into the heat exchanger 120 at an annular side inlet 132 (see FIG. 8A). As the process fluid moves down the annular side of the heat exchanger 120 it is pre-heated by the gas stream (arrow K) moving up through the air passages 130 and by the product fluid moving up the tube side of the heat exchanger 120. As shown by arrow M', the process fluid exits the heat exchanger 120 at an annular side outlet 121 and enters a reactor inlet 123. As the process fluid moves through the coils of the reactor 122, it is heated to the process temperature by the gas stream (arrow K) moving up through the air passages 130. As shown by arrow N, the processed fluid or product exits the reactor 122 via a reactor outlet 134 and re-enters the heat exchanger 120 through a tube side inlet 135. As it moves up the tube side, the product fluid is cooled by the process fluid flowing down the annular side of the heat exchanger 120. The product fluid exits the heat exchanger 120 through a tube side outlet 136.

Figure 9:
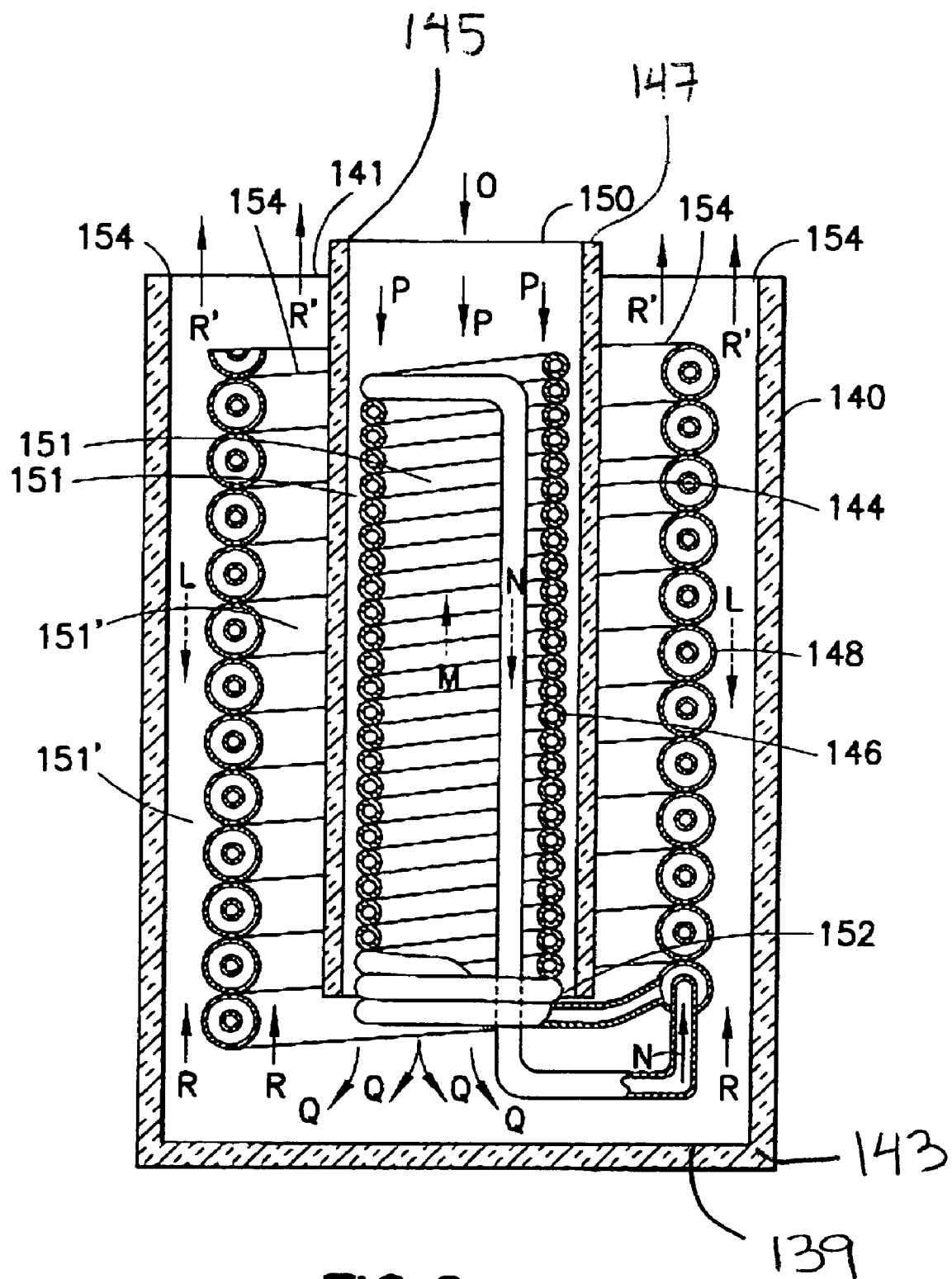
FIG. 9 is a sectional plan side view of a further version of the processor assembly of a fluid processor embodying features of the present invention.

FIG. 9 is another version of the processor assembly of a fluid processor embodying feature of the present invention. The processor assembly comprises a heat exchanger 148 and a reactor 146 which are the same as those of the processor assembly of FIG. 8A. However, in this version the heat exchanger 148 is contained in an insulated enclosure 140 having an opening 141 only at the top. Further, the reactor 146 is disposed within a hot gas tube 144 and the hot gas tube 144 is, in turn, nested within the heat exchanger 148. The enclosure 140 is fabricated in the same way as the duct 124 of the processor assembly in FIG. 8A. Preferably, the enclosure 140 comprises a support structure 139 fabricated from materials resistant to high temperature oxidizing environments such as nickel, chromium, or iron alloys, or ceramic materials. The structure 139, in turn, is covered by one or more layers 143 of the insulating material. The enclosure is dimensioned to allow it to completely enclose the bottom of the heat exchanger and the sides of the heat exchanger but still leave space for air passages 151' and room to allow for expansion of the heat exchanger 148. The enclosure has an opening 141 at the top having a sufficient size to allow the heat exchanger 148 to be inserted into the enclosure 140. The hot gas tube 144 has a tube inlet 150 at the top and a tube outlet 152 at bottom. Preferably, the tube 144 comprises a support structure 145 fabricated from materials resistant to high temperature oxidizing environments such as nickel, chromium, or iron alloys, or ceramic materials. The structure 145, in turn, is covered by one or more layers 147 of the insulating material previously described above. Further, the tube 144 is dimensioned to allow it to enclose the coils of the reactor 146 but still allow room for air passages 151 and 151'.

In operation, the process fluid and the product fluid move through the processor assembly in the same manner described above with respect to the processor assembly of FIG. 8A. However, unlike the processor assembly of FIG. 8A, the hot gas stream (arrow 0) is introduced through the inlet 150 of the hot gas tube 144. The hot gas stream moves down air passages 151 between the reactor 146 and hot gas tube 144 (see, arrow P). The gas stream exits (see, arrow Q) from the outlet 152 and moves upwards (see, arrow R) through air passages 151' formed between the enclosure 140 and heat exchanger 148 and between the heat exchanger 148 and hot gas tube 144. The gas stream exits the processor assembly (see, arrow R') via openings or vents 154 formed by the spaces between the top edges of the enclosure 140 and top of the heat exchanger 148 and the spaces between the top of the heat exchanger 148 and top of the hot gas tube 144.

Using the nested configurations described above, a minimum amount of energy is necessary to change the temperature of a fluid continuously flowing through the reactor and heat exchangers. The nested configurations of the processor assemblies described above place the hottest (i.e., a heater) or the coldest (i.e., a cooler) component in the center, thereby reducing ambient heat loss or heat gain respectively. As such, the nested configurations of the processor assemblies described above would be more efficient than a processor assembly whose components, e.g., the heat exchanger heater and reactor, are not nested together or have been individually insulated. In addition to requiring less energy to operate, the preferred embodiments of the invention use FDA recommended tube-in-tube heat exchangers. Thus, batch validation of the SWFI product is not required. This is in contrast to other fluid processors for making SWFI that do not use FDA recommended heat exchangers (e.g., plate and frame heat exchangers) which require batch validation for SWFI production.

Figure 12A:
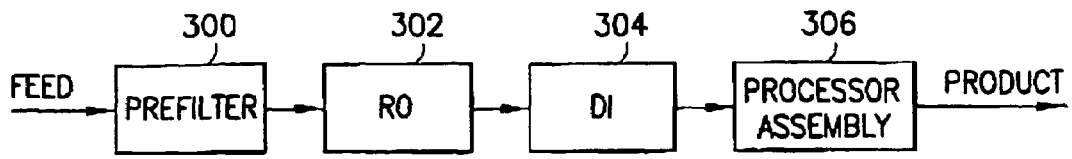
FIGS. 12A to 12F are block diagrams showing different versions of a treatment assembly of the processor assembly embodying features of the present invention.
Figure 12B:
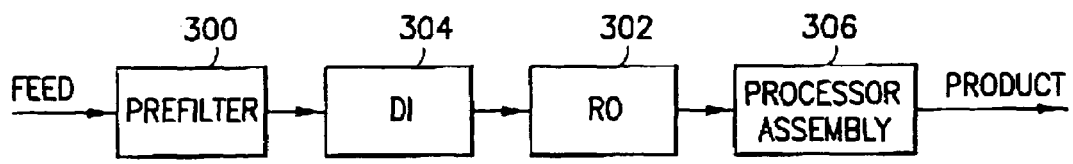
Figure 12C:
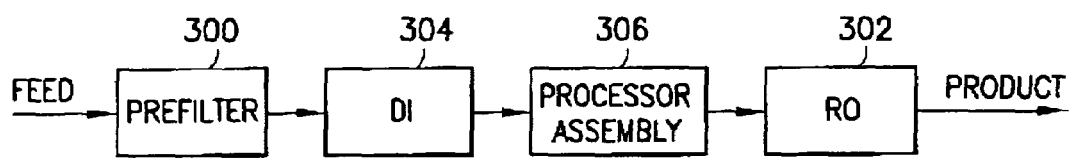
Figure 12D:
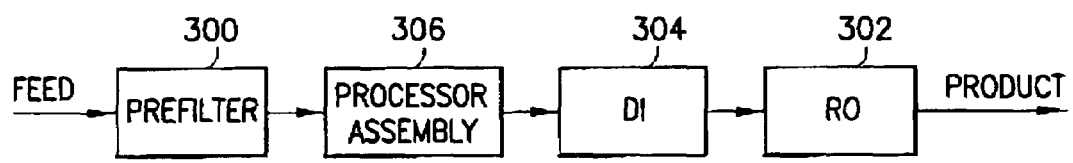
Figure 12E:
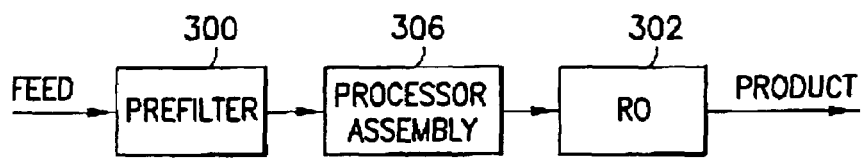
Figure 12F:
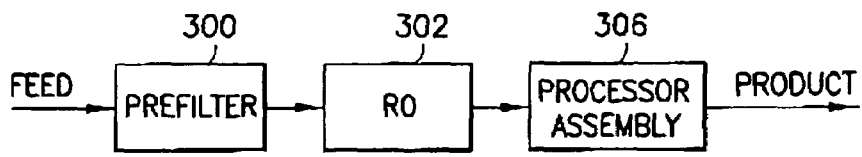

Another aspect of the present invention is a treatment assembly comprising a variety of combinations of filters, reverse osmosis and ion exchange devices acting in conjunction with the processor assembly to achieve a product quality that meets specific requirements. In a preferred embodiment of the present invention (see, FIG. 1A), the treatment assembly 200 comprises a combination of a prefilter 202 (e.g., an activated carbon filter), a reverse osmosis (RO) device 204, and an ion exchange (DI) 206 device which are all disposed upstream of the processor assembly. The combination of the last two devices is known as RODI, hereafter "RODI apparatus". The RO device 302 may be disposed immediately upstream of the DI device 304 (see, FIG. 12A) or immediately downstream of the DI device 304 (see, FIG. 12B). Referring to FIG. 11A, as previously discussed above, the RO device 204 may also function as the flow splitter 204 (see above) of the process control system 210. Additional filters may also be placed at other locations in the fluid processor. The treatment assembly removes suspended and dissolved solids, oxidizable substances, and dissolved gases from the fluid when such a step is required in order to produce a particular product fluid (e.g., SWFI). In addition, the removal of the foregoing materials from the fluid ensures that fouling in the fluid processor is minimized. In an alternative embodiment, the treatment assembly comprises only the prefilter 300 and the RO device 302 wherein the RO device 306 is disposed downstream of the processor assembly 306 (see, FIG. 12E) or upstream of the processor assembly (see, FIG. 12F). In further alternative embodiments, the RO device 302 (see, FIG. 12C) or both the RO device 302 and the DI device 304 (see, FIG. 12D) may be disposed downstream of the processor assembly 306.

A further aspect of the present invention is a sanitization assembly for the in situ sanitization during start-up and shutdown of the fluid processor. See, FIGS. 10A to 11B. For simplicity, the process control system is not shown in FIGS. 10A, 10B and 11B. The sanitization assembly comprises an isolation valve 168, a drain valve 190 (see, FIG. 11A and B), and a start-up loop (see, FIGS. 10A and 10B) comprised of a start-up loop flow restrictor 160 and a four-way valve 162 having a startup position and a normal position. Referring to FIG. 10A and 10B, the isolation valve 184 is located downstream of a fluid source 166 and upstream of the pump 170 and allows for isolating the system from the fluid source 166. The drain valve 190 (see, FIG. 11A and 11B) is located upstream of the processor assembly 181 and at the lowest point of the fluid processor. The drain valve allows for draining fluid from the system. The startup flow restrictor 160 (see, FIGS. 10A and 10B) controls the flow rate through the startup loop. The startup flow restrictor 160 is located immediately downstream of the isolation valve 184 along a first fluid path that is separate from but running parallel to a second fluid path going from the isolation valve 184 to the pump 170. The four way valve 162 is disposed downstream of the flow restrictor 160 and the pump 170.

The four-way valve 162 has a first connection for receiving fluid from the startup flow restrictor 160, a second connection for directing fluid from the startup flow restrictor directly to a reactor 172, a third connection for receiving fluid from the pump 170, and a fourth connection for directing the fluid from the pump to the heat exchanger 174. In the startup position (see, FIG. 10A), the four way valve 162 directs the fluid from the startup flow restrictor 160 to the reactor 172 through the first and second connection. In the normal position (see, FIG. 10B), the four-way valve directs fluid from the pump 170 to the heat exchanger 174 through the third and fourth connection.

For sanitization during startup, a fluid inlet 164 is connected to the fluid source 166 which has a minimum line pressure of not less than about 10 psia and not greater than about 800 psia (e.g. a tap water line). The four-way valve 162 is then switched to its start-up position and the isolation valve 184 is opened. Instead of activating the pump 170, the fluid is driven by line pressure to enter the reactor 172 at a small flow rate that is regulated by the start-up loop flow restrictor 160. A heater 176 is switched on and, as the reactor 172 heats up, steam is generated for sterilizing the system. This steam goes through the inner side of the heat exchanger 174 and flows downstream of the processor assembly to exits at a fluid outlet 178. After steam has gone through the fluid outlet 178 for a period of time sufficient to sterilize the system, the four-way valve 162 is switched to its normal position (see, FIG. 10B). The pump 170 is then turned on and the fluid processor is allowed to stabilize at the desired temperature and pressure for period of time before product is collected from the fluid outlet 178.

Figure 11B:
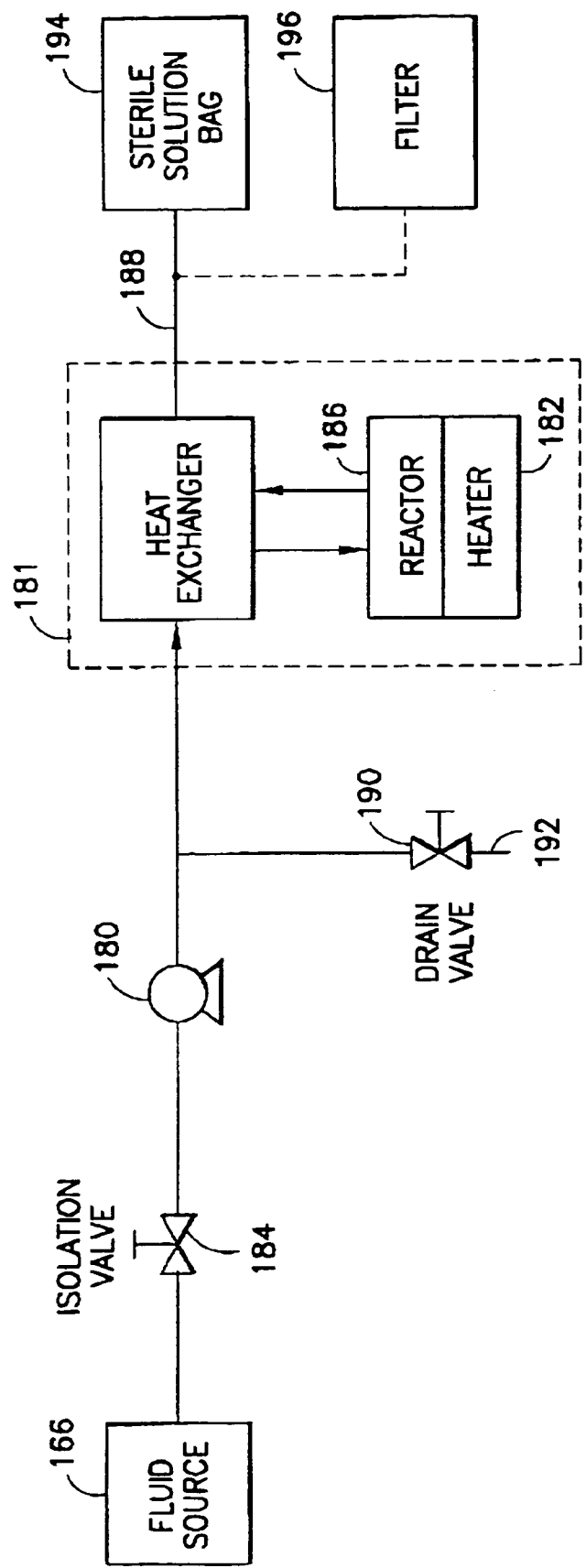
FIG. 11B is block diagram of the fluid processor of FIG. 11A in storage condition.

The sterilization procedure during shutdown is as follows. See FIGS. 11A and 11B. The pump 180 and heater 182 are turned off. The isolation valve 184 from the fluid source 186 to the system is turned off. As the fluid in the fluid processor components that are downstream of the reactor 186 is expelled through the fluid outlet 188 by the pressure of the steam generated by the residual heat of the reactor 186, the drain valve 190 is opened to discharge fluid in the fluid processor components that are upstream of the processor assembly 181 (see, arrow S). After the fluid ceases to flow from the fluid outlet 188, a bag 194 (or, alternatively, a syringe) containing a sufficient amount of sterile solution is connected to fluid outlet 188, and the drain valve 190 is closed. See, FIG. 11B. For simplicity, the components of the process control system 210 and treatment assembly 200 of FIG. 11A are not shown in FIG. 11B. Examples of suitable sterile solutions are a greater than about 50% aqueous solution of isopropyl alcohol or a dilute hydrogen peroxide solution. As the system cools down and the steam within the fluid processor condenses, a partial vacuum is created which causes the sterile solution in the bag 194 to be drawn into the fluid processor to fill up the internal volume of the system. The bag 194 is left on the fluid output 188 while the fluid processor is stored away until the next use. Referring to FIG. 11B, an alternative approach (shown in dotted line) is to use a filter 194 (e.g., a HEPA filter) to end cap the fluid output 188. The filter allows air to pass through and functions as a barrier to prevent any airborne contaminants from getting into the system.

In a further aspect of the present invention, the fluid processor has an electronic control system to provide operator input and to make it convenient for an untrained person to operate the fluid processor. The electronic control system comprises an operator interface (e.g., a touch screen liquid crystal display or LCD) for providing readouts and operator input connected to a programmable logic controller ("PLC") that manages the electronic control system. The PLC comprises a central processing unit and a main circuit control and may be interfaced with temperature sensors, pressure sensors, a temperature controller (e.g., a heater or cooler control), a pump controller and other similar sensors and controllers that are connected to or located in the fluid processor. The PLC can be programmed for specific applications such as turning on/turning off the heater, cooler, or pump when a target temperature and/or pressure are reached. The main control circuit has a temperature feedback circuit that turns off the heater or cooler if an over-temperature or under-temperature condition is detected by the sensors. Similarly, the pump is turned off if an over-pressure condition is detected by the sensors. The control system can also include error switches that detect various error conditions. Upon an error condition being detected, the pump and/or the heater or cooler are shut down and instructions for service or troubleshooting are displayed at the touch screen interface.

Figure 13:
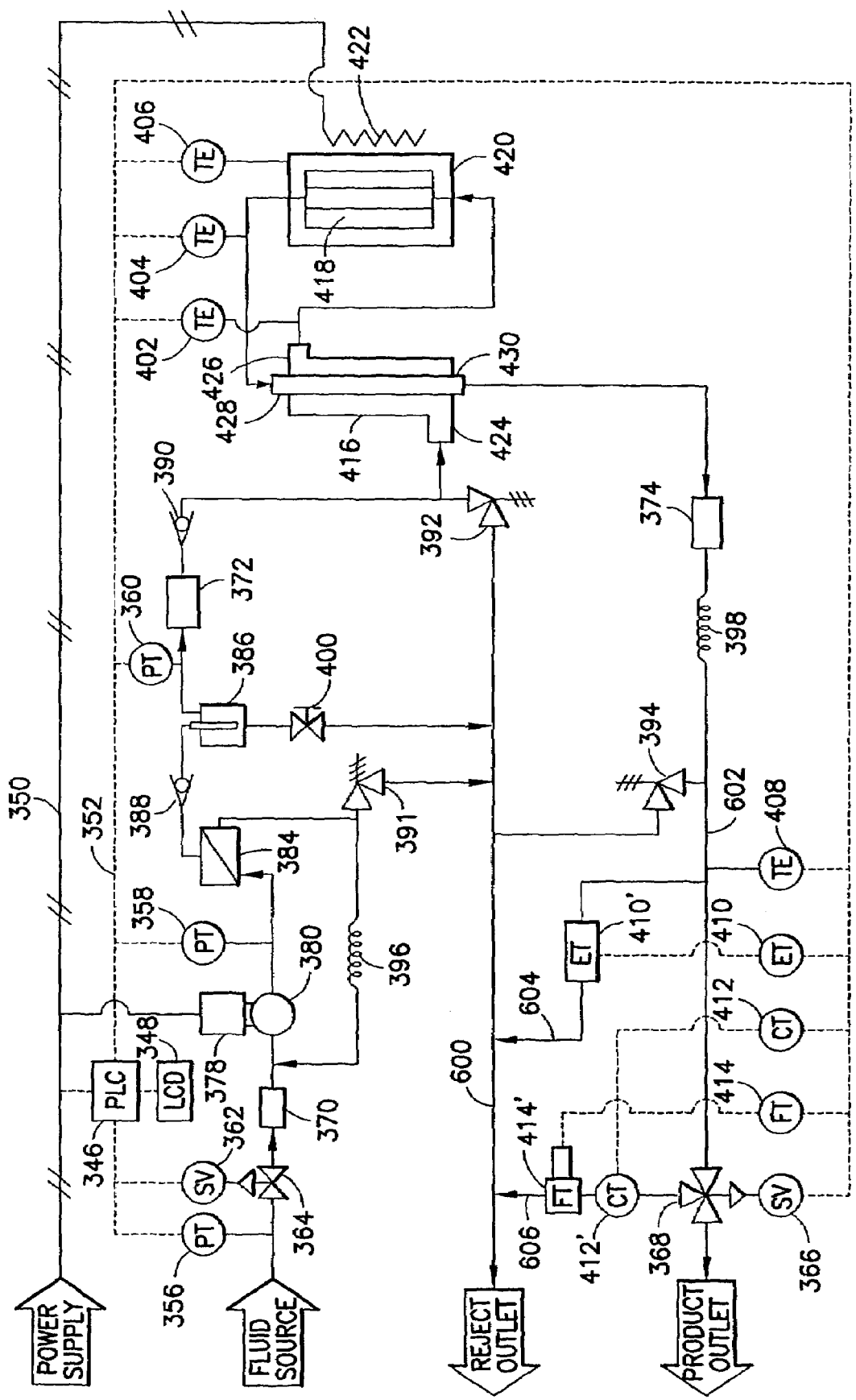
FIG. 13 is a block diagram of an electronic control system of a fluid processor embodying features of the present invention.

One version of the electronic control system of a fluid processor embodying features of the present invention is shown is FIG. 13. The electronic control system comprises an LCD touch screen device 348 interfaced with a PLC 346. The PLC is interfaced via a circuit 352 with the following devices: a first, second and third pressure transducer 356, 358 and 360; an isolation valve solenoid 362; a three-way valve solenoid 366; a first, second, third and fourth temperature sensors 402, 404, 406 and 408; an endotoxin sensor 410' having a signal conditioner 410, a conductivity meter 412 having a conductivity cell 412'; and a flow meter 414 having a flow sensor 414'.

In operation, the isolation valve solenoid 362 opens an isolation valve 364 to allow a pump 380 which is operated by a pump motor 378 to draw and pressurize the fluid from a fluid source through the isolation valve 364 and a first filter 370 (i.e., a prefilter). From the pump 380, the fluid passes through a RODI apparatus comprising a reverse osmosis device 384 and an ion exchange device 386. The reverse osmosis device 384 also functions as a flow splitter and diverts a portion of the fluid from the pump 380 to form a recirculation loop flowing through a pressure relief valve 391 and a first flow restrictor 396. The undiverted portion of the fluid goes through a second filter 372 and enters a heat exchanger 416 via an annular side inlet 424 where it is pre-heated by fluid counter-currently flowing through the tube side. The pre-heated fluid exits the heat exchanger 416 at a tube side outlet 426 and enters a reactor 418 that is contained within a temperature homogenizer 420. A heater 422 connected to a power supply via a power line 350 heats the fluid in the reactor 418 to the process temperature.

Pressure transducers 356, 358, and 360 and temperature sensors 402, 404, 406 and 408 located at various points of the fluid processor respectively measure the pressure and temperature of the fluid and send their readings to the PLC 346 via the circuit 352. Check valves 388 and 390 prevent any fluid from flowing back upstream. Further, second and third pressure relief valves 392 and 394 provide added safety by opening up when the pressure of the fluid exceeds a certain level. When pressure relief valves 391, 392, and 394 open, the fluid from these valves flows to a reject outlet via a reject line 600 for disposal. Any fluid from a drain valve 400 also flows to the reject outlet.

From the reactor 418, the processed fluid (i.e. product fluid) re-enters the heat exchanger 416 via a tube side inlet 428 and is cooled by the fluid counter-currently flowing in the annular side. The product fluid exits the heat exchanger 416 at a tube side outlet 430 and passes through a third filter 374 and a second flow restrictor 398. A portion of the product fluid from the second flow restrictor is diverted to pass through an endotoxin sensor 410' so that the endotoxin level of product fluid can be measured and the endotoxin level readings are sent to the PLC 348 via the signal conditioner 410 and circuit 352. The product fluid then passes through a three-way valve 368 and is collected at a product outlet.

If it is desired to measure the flow rate of the processed fluid coming from the reactor or to measure its conductivity, the flow of the product fluid is diverted from the product outlet so as to flow along a divert line. In the embodiment shown in FIG. 13, the three-way valve solenoid 366 activates the three-way valve 368 to divert the product fluid from the product outlet to the reject outlet through a divert line 606 flowing from the three-way valve 368 to the reject outlet. It is to be understood, however, that diverting the product fluid from the product outlet to the divert line by means or devices other than using a three-way valve is within the spirit of the present invention. As the product fluid flows along the divert path, the conductivity meter 412 and flow meter 414 respectively measure flow rate and conductivity of the product fluid as the product fluid passes through the conductivity cell 412' and a flow sensor 414' which are disposed along the divert line. The readings of the conductivity meter 412 and flow meter 414 are then sent through the circuit 352 to the PLC 346. Alternatively, the endotoxin sensor 410' may also be disposed along the divert line.

In an alternative embodiment (not shown), the endotoxin sensor 410', the flow sensor 414' or the conductivity cell 412' or any two or all three of the foregoing devices may be disposed along a fluid path flowing downstream from the processor assembly to the product outlet, hereafter, a "product line". In a further alternative embodiment (not shown) the endotoxin sensor 410', the flow sensor 414' or the conductivity cell 412' or any two or all three of the foregoing devices may be disposed along a flow path flowing downstream from the processor assembly and running parallel to the product line, hereafter a "discharge line".

Figure 4:
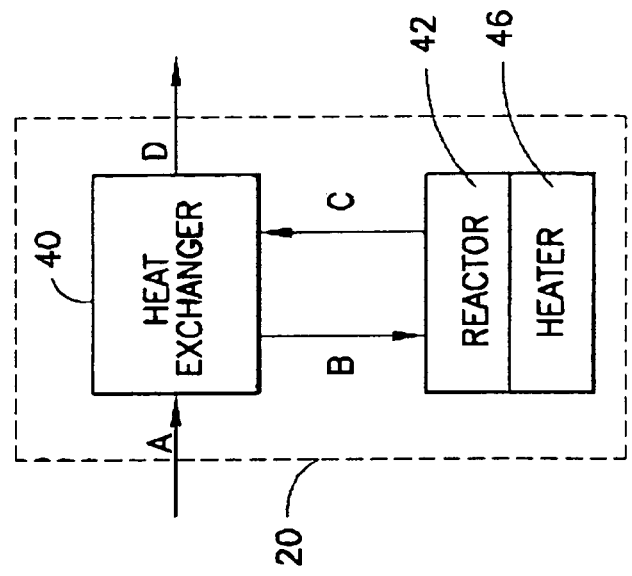
FIG. 4 is a block diagram of a processor assembly for use with the fluid processor of FIG. 3.

A specific application of the preferred embodiment of the present invention is the production of SWFI from water (i.e. "feed water"). Referring to FIGS. 3 and 4, in producing SWFI, the pressure relief valve 32 is adjusted to a setting, which, in combination with the pump output pressure and the settings of the flow restrictors 28 and 30, will produce a pressure in the processor assembly 20 that will allow the feed water to be heated to a temperature well above its normal boiling point without causing surface boiling which may destabilize the process and more critically demand higher energy input. Surface boiling refers to boiling at the heating surface on a microscopic level as opposed to the boiling in the bulk phase. Surface boiling is avoided because, although heating the feed water results in phase change (i.e., liquid to gas) of the feed water at the gas-liquid interface, the process control system (see below) maintains the pressure of the feed water at or near the saturation point of the feed water for given temperature. Thus, the phase change of the water is rapidly quenched by the bulk (i.e. liquid) phase of the water.

The feed water must remain in the reactor 40 for a period of time (i.e. "holding time") sufficient to depyrogenate and sterilize the water. The holding time required is a function of the highest temperature that water reaches. Obviously, the highest temperature occurs in the reactor 40, which is heated by the heater 46. The higher the water temperature, the less holding time is required. Examples of the temperature and time correlation for depyrogenation can be found in U.S. Pat. No. 6,585,890 to Li et al., "Process for Producing Sterile Water for Injection from Potable Water", which is incorporated herein by reference. Since depyrogenation requires higher temperature and/or longer time than sterilization, a temperature/time correlation established for depyrogenation should suffice for sterilization of water. Typically, in depyrogenation, for a given fluid processor the volume of the reactor is selected to accommodate a desired fluid throughput, which in turn is determined by survival curves. Survival curves are graphs wherein the logarithm of pyrogen concentration is plotted against holding time for each given temperature. Since the average holding time equals the volume of the reactor divided by the volumetric flow rate of the fluid, the process control system, by controlling the density (i.e., temperature and pressure) of the feed water, ensures that the appropriate holding time required for reducing the pyrogen concentration of the feed water to the desired level is met.

The present invention allows for the continuous production of SWFI that meets the requirements contained in the United States Pharmacopoeia XXIV and FDA regulations. Specifically, the treatment of the feed water by the treatment assembly ensures that the final product meets regulatory requirements for SWFI as to removal of particulate matter, oxidizable substances, dissolved gases, metals and electrolytes. As for depyrogenation and sterilization requirements, these are met by HTP treatment of the feed water. Moreover, since the processor assembly processes feed water at high temperatures, this results in extremely short treatment times required for sterilization and depyrogenation.

The present invention provides an apparatus and method for process control that is suitable for the depyrogenation and production of SWFI using a hydrothermal process. Depyrogenation of water using the present invention does not require depyrogenation agents. The HTP treatment destroys pyrogens by high-temperature heat instead of simple physical separations as in filtration and distillation methods. Also, the use of a combination of simple devices such as flows restrictors and a compact arrangement of heat exchangers and reactors allows for a compact, reliable fluid processor having low energy requirements. Further, the present invention includes a sanitization assembly and method that makes the fluid processor easy to maintain and operate. Thus, the present invention obtains a fluid processor that is well suited for use under field conditions. Although the invention has been described with reference to preferred embodiments, it will be appreciated by one of ordinary skill in the art that numerous modifications are possible in light of the above disclosure. For example, although the preferred embodiments of the present invention relates to a fluid processor for producing SWFI, the concepts of this invention may be may find a broad range of applications in systems and apparatus that have processing requirements similar to the production of SWFI or which require control and/or stabilization of a fluid process.

What is claimed is:

1. A fluid processor comprising:
   a pump for drawing a fluid from a fluid source through a fluid inlet and pressurizing the fluid;
   a processor assembly for processing the fluid from the pump, the processor assembly comprising:
      a heat exchanger for recovering thermal energy;
      a reactor for processing a fluid by heating:
      and a heater for heating the reactor;
   a process control system comprising: a flow splitter disposed between the pump and the processor assembly for diverting a portion of the fluid from the pump, a first flow restrictor for receiving the diverted fluid and directing the diverted fluid to the fluid inlet, a pressure relief valve disposed between the first flow restrictor and the flow splitter, and a second flow restrictor disposed downstream of the processor assembly, wherein the flow splitter, first flow restrictor, second flow restrictor and pressure relief valve are constructed and arranged to coact with each other to control the pressure and flow rate of the fluid in the fluid processor;
   a sanitization assembly comprising:
      an isolation valve disposed immediately downstream of the fluid inlet
      a drain valve disposed at the lowest point of the fluid processor and between the pump and the processor assembly; and
   a startup loop assembly comprising:
      a first fluid path running from the isolation valve to the reactor;
      a second fluid path running from the isolation valve to the pump;
      a startup flow restrictor disposed immediately downstream of the isolation valve and positioned along the first fluid path; and
      a four-way valve disposed immediately downstream of the startup flow restrictor and the pump, the four-way valve-having
         a first connection for receiving fluid from the startup flow restrictor,
         a second connection for directing fluid from the startup flow restrictor to the reactor,
         a third connection for receiving fluid from the pump, and
         a fourth connection for directing the fluid from the pump to the heat exchanger, and further,
         wherein the four-way valve has a startup position for directing fluid from the startup flow restrictor to the reactor through the first and second connection and a normal position for directing the fluid from the pump to the heat exchanger through the third and fourth connection.

2. The fluid processor of claim 1, wherein startup flow restrictor is a fixed setting flow restrictor.

3. The fluid processor of claim 1, wherein the startup flow restrictor is an adjustable setting flow restrictor.

4. A method for sanitizing the fluid processor of claim 1 during startup, the method comprising:
   connecting the fluid inlet to the fluid source wherein the fluid source has a line pressure of not less than about 10 psia and not greater than about 800 psia,
   switching the four-way valve to the startup position;
   opening the isolation valve;
   introducing fluid into the fluid processor at line pressure;
   switching on the heater;
   allowing steam generated by the heater to flow downstream of the reactor and exit at a fluid outlet; and
   switching the four-way valve to the normal position.

5. A method for sanitizing the fluid processor of claim 1 during shutdown and storage, the method comprising:
   turning off the pump and heater;
   closing the isolation valve;
   allowing residual heat of the reactor to produce steam from the fluid in the processor assembly;
   allowing the steam to generate a pressure in the processor assembly;

allowing the pressure to expel the fluid that is downstream of the processor assembly out through a fluid outlet;

opening the drain valve to discharge the fluid that is upstream of the processor assembly;

attaching a closure means to the fluid outlet when fluid ceases to flow from the fluid outlet and closing the drain valve when the fluid ceases to flow from the drain valve.

6. The method of claim 5, wherein the closure means is a container holding a sterile solution.

7. The method of claim 5, wherein the closure means is a filter.

8. The fluid processor of claim 1, wherein the heat exchanger is a shell-and-tube heat exchanger and further, wherein a process fluid flows through a shell side of the heat exchanger and a product fluid flows through a tube side of the heat exchanger.

9. The fluid processor of claim 1, wherein the heat exchanger is a tube-in-tube heat exchanger and further, wherein a process fluid flows through an annular side of the heat exchanger and a product fluid flows through a tube side of the heat exchanger.

10. The fluid processor of claim 9, wherein the heat exchanger is a helical coil tube-in-tube heat exchanger.

11. The fluid processor of claim 10, wherein the reactor and the heater are nested within the heat exchanger.

12. The fluid processor of claim 11, wherein the reactor and the heater are disposed within a temperature homogenizer.

13. The fluid processor of claim 12, wherein the temperature homogenizer comprises a multiplicity of blocks, the blocks being joined together by fasteners.

14. The fluid processor of claim 12, wherein the temperature homogenizer is a unitary structure produced by casting and further, wherein the reactor is formed as an integral pan of the temperature homogenizer.

15. The fluid processor of claim 12, wherein the temperature homogenizer is enclosed by an insulation jacket.

16. A fluid processor comprising:
a pump for drawing a fluid from a fluid source through a fluid inlet and pressurizing the fluid;
a processor assembly comprising a fluid heater for heating the fluid from the pump;
a process control system comprising: a flow splitter disposed between the pump and the processor assembly for diverting a portion of the fluid from the pump, a first flow restrictor for receiving the diverted fluid and directing the diverted fluid to the fluid inlet, a first pressure relief valve disposed between the first flow restrictor and the flow splitter, a second pressure relief valve disposed between an upstream side of the processor assembly and a downstream side of the flow splitter and a second flow restrictor disposed downstream of the processor assembly,
wherein the flow splitter, flaw restrictors and pressure relief valves are constructed and arranged to coact with each other to control the pressure and flow rate of the fluid in the fluid processor.

17. The fluid processor of claim 16, wherein the process control system maintains the pressure of the fluid in the processor assembly at least about the saturation point of the fluid at a predetermined temperature.

18. The fluid processor of claim 16, wherein the flow splitter is a filtration device.

19. The fluid processor of claim 16, wherein the flow splitter is a reverse osmosis device.

20. The fluid processor of claim 16, wherein at least one flow restrictor is a fixed setting flow restrictor.

21. The fluid processor of claim 20, wherein the fixed setting flow restrictor is a fixed length capillary tube.

22. The fluid processor of claim 16, wherein at least one flow restrictor is an adjustable setting flow restrictor.

23. The fluid processor of claim 22, wherein the adjustable setting flow restrictor is a metering valve.

24. The fluid processor of claim 16, wherein at least one pressure relief valve is a spring-loaded adjustable pressure relief valve.

25. The fluid processor of claim 16, wherein the fluid processor further comprises a check valve disposed upstream of the processor assembly.

26. The fluid processor of claim 16, further comprising a treatment assembly comprising a prefilter disposed upstream of the processor assembly.

27. The fluid processor of claim 26, wherein the treatment assembly further comprises a reverse osmosis device disposed downstream of the prefilter.

28. The fluid processor of claim 26, wherein the treatment assembly further comprises a RODI apparatus disposed between the prefilter and the processor assembly, the RODI apparatus comprising a reverse osmosis device and an ion exchange device.

29. The fluid processor of claim 26, wherein the treatment assembly further comprises a RODI apparatus disposed downstream of the processor assembly, the RODI apparatus comprising a reverse osmosis device and an ion exchange device.

30. The fluid processor of claim 26, wherein the treatment assembly further comprises a RODI apparatus comprising: an ion exchange device disposed between the prefilter and processor assembly; and a reverse osmosis device disposed downstream of the processor assembly.

31. The fluid processor of claim 16, wherein fluid processor processes feed water to produce sterile water for injection.

32. The fluid processor of claim 16, further comprising:
a temperature sensor for measuring the temperature of the fluid in the processor assembly; and
a controller for controlling the fluid heater.

33. The fluid processor of claim 16, further comprising an electronic control system for controlling the fluid processor, the electronic control system comprising:
a touch screen interface for providing readouts and operator input; and
a programmable logic controller for managing the electronic control system, the programmable logic controller comprising a main control circuit and a central processing unit and further, wherein the programmable logic controller is interfaced with a temperature sensor, a pressure transducer, a controller for controlling the fluid heater, and a pump controller.

34. The fluid processor of claim 33, wherein the programmable logic controller is further interfaced with an endotoxin sensor having a signal conditioner, a flow rate meter having a flow sensor, and a conductivity meter having a conductivity cell.

35. The fluid processor of claim 34, wherein the endotoxin sensor, flow sensor and conductivity cell are disposed downstream of the processor assembly along a discharge line.

36. The fluid processor of claim 34, wherein the flow sensor and conductivity cell are disposed downstream of the processor assembly along a divert line.

37. The fluid processor of claim 34, wherein the endotoxin sensor, flow sensor and conductivity cell are disposed along a divert line.

38. The fluid processor of claim 34, wherein the endotoxin sensor is disposed along a sampling line.

39. The fluid processor of claim 16, wherein the heater is a hot gas heater and further, wherein the processor assembly further comprises:
   a helical coil tube-in-tube heat exchanger for exchanging heat between a process fluid and a product fluid; and
   a helical coil-shaped reactor nested within the heat exchanger.

40. The fluid processor of claim 39, wherein the processor assembly further comprises an insulated duct having a hot gas inlet at one end and a vent at the other end and further, wherein the heat exchanger is disposed within the insulated duct.

41. The fluid processor of claim 39, wherein the processor assembly further comprises a hot gas tube and an insulated enclosure having an opening at the top and further, wherein the heat exchanger is disposed within the enclosure and the reactor is disposed within the hot gas tube and further, wherein the hot gas tube is nested within the heat exchanger.

42. The fluid processor of claim 16, wherein the processor assembly further comprises a multiplicity of heat exchangers for exchanging heat between a process fluid and a product fluid.

43. The fluid processor of claim 42, wherein at least two heat exchangers are connected together in parallel.

44. The fluid processor of claim 42, wherein at least two heat exchangers are connected together in series.

45. The fluid processor of claim 42, wherein at least one heat exchanger is a tube-in-tube type heat exchanger.

46. The fluid processor of claim 42, wherein at least one heat exchanger is a helical coil tube-in-tube type heat exchanger.

47. The fluid processor of claim 42, wherein at least one heat exchanger is a rope rug coil tube-in-tube heat exchanger.

48. The fluid processor of claim 16 further comprising:
   a temperature sensor for measuring the temperature of the fluid upstream of the processor assembly.

49. The fluid processor of claim 16 further comprising:
   a temperature sensor for measuring the temperature of the fluid downstream of the processor assembly.

50. The fluid processor of claim 16 further comprising:
   a pressure sensor for measuring the pressure of the fluid upstream of the processor assembly.

51. The fluid processor of claim 16 further comprising:
   a pressure sensor for measuring the pressure of the fluid downstream of the processor assembly.

52. The fluid processor of claim 16, wherein the process control system further comprises a third pressure relief valve disposed downstream of the second flow restrictor.

* * * * *